US009782258B2

(12) United States Patent
Sabbah et al.

(10) Patent No.: US 9,782,258 B2
(45) Date of Patent: Oct. 10, 2017

(54) INTRAMYOCARDIAL PATTERNING FOR GLOBAL CARDIAC RESIZING AND RESHAPING

(75) Inventors: Hani N. Sabbah, Waterford, MI (US); Randall J. Lee, Hillsborough, CA (US); Andrew G. Hinson, Washington, DC (US)

(73) Assignees: THE REGENTS OF THE UNIVERSITY OF CALIFORNIA, Oakland, CA (US); CARDIOPOLYMERS, INC., Laguna Hills, CA (US); HENRY FORD HEALTH SYSTEM, Detroit, MI (US)

( * ) Notice: Subject to any disclaimer, the term of this patent is extended or adjusted under 35 U.S.C. 154(b) by 1117 days.

(21) Appl. No.: 11/900,005

(22) Filed: Sep. 7, 2007

(65) Prior Publication Data
US 2008/0065048 A1 Mar. 13, 2008

Related U.S. Application Data

(60) Provisional application No. 60/843,475, filed on Sep. 8, 2006.

(51) Int. Cl.
*A61M 37/00* (2006.01)
*A61F 2/24* (2006.01)
(Continued)

(52) U.S. Cl.
CPC .......... *A61F 2/2451* (2013.01); *A61F 2/2481* (2013.01); *A61K 9/0024* (2013.01);
(Continued)

(58) Field of Classification Search
CPC ........ A61F 2002/249; A61F 2250/0067; A61F 2/2481; A61F 2/2478; A61F 2/2451;
(Continued)

(56) References Cited

U.S. PATENT DOCUMENTS 5,002,067 A 3/1991 Berthelsen et al.
5,324,325 A 6/1994 Moaddeb
(Continued)

FOREIGN PATENT DOCUMENTS

JP 2004-533294 A 11/2004
WO 9716170 A1 5/1997
(Continued)

OTHER PUBLICATIONS

Carpenter, William R., Office action in U.S. Appl. No. 11/899,962, filed Sep. 7, 2007, dated Jun. 4, 2009, 14 pages.
(Continued)

*Primary Examiner* — Imani Hayman
(74) *Attorney, Agent, or Firm* — PATNSTR, APC; Peter Jon Gluck

(57) ABSTRACT

Cardiomyopathy may be treated by distributing space-occupying agent within the myocardium in a pattern about one or more chambers of the heart, such that the space-modifying agent integrates into and thickens at least part of the cardiac wall about the chamber so as globally to reduce wall stress and stabilize or even reduce chamber size. Some patterns also cause a beneficial global reshaping of the chamber. These changes occur quickly and are sustainable, and have a rapid and sustainable therapeutic effect on cardiac function. Over time the relief of wall stress reduces oxygen consumption and promotes healing. Moreover, various long-term therapeutic effects may be realized depending on the properties of the space-occupying agent, including combinations with other therapeutic materials. Specific cardiac conditions treatable by these systems and methods include, for example, dilated cardiomyopathy (with or without overt aneurismal formations), congestive heart failure, and ventricular arrhythmias. Patterns of distribution of space-occupying agent within the myocardium for global
(Continued)

resizing may also be used or augmented to treat localized conditions such as myocardial infarctions, overt aneurysm of the ventricular wall as typically forms in response to large transmural myocardial infarctions, and mitral regurgitation due to a noncompliant mitral valve. These techniques may also be used to treat localized conditions that may not yet have progressed to cardiomyopathy.

21 Claims, 24 Drawing Sheets

(51) Int. Cl.
    *A61L 27/38*    (2006.01)
    *A61K 9/00*    (2006.01)
    *A61L 27/20*    (2006.01)
    *A61L 27/52*    (2006.01)
    *A61M 5/14*    (2006.01)
    *A61M 5/178*    (2006.01)

(52) U.S. Cl.
    CPC .......... *A61L 27/20* (2013.01); *A61L 27/3873* (2013.01); *A61L 27/52* (2013.01); *A61M 5/14* (2013.01); *A61M 5/178* (2013.01); *A61M 37/00* (2013.01); *A61M 37/0069* (2013.01); *A61F 2002/249* (2013.01); *A61F 2250/0067* (2013.01); *A61L 2400/06* (2013.01)

(58) Field of Classification Search
    CPC ........ A61B 17/00491; A61B 17/12022; A61B 17/12045; A61B 17/12122; A61B 17/12136; A61B 17/12181; A61B 17/12186; A61B 17/1219; A61B 2017/00243; A61B 2017/048; A61B 2017/1205; A61B 2017/12127; A61L 31/005; A61L 2400/06; A61L 27/20; A61L 27/3873; A61L 27/52; A61K 9/0024; A61M 37/00; A61M 37/0069; A61M 5/14; A61M 5/178
    USPC .............. 604/511, 522, 93.01; 424/484–488
    See application file for complete search history.

(56) References Cited

U.S. PATENT DOCUMENTS

| | | | |
|---|---|---|---|
| 5,419,777 A | 5/1995 | Hofling | |
| 5,447,533 A | 9/1995 | Vachon et al. | |
| 5,531,780 A | 7/1996 | Vachon | |
| 5,551,427 A | 9/1996 | Altman | |
| 6,063,061 A | 5/2000 | Wallace et al. | |
| 6,132,451 A | 10/2000 | Payne et al. | |
| 6,238,406 B1 | 5/2001 | Ellis et al. | |
| 6,334,968 B1 | 1/2002 | Shapiro et al. | |
| 6,360,749 B1 | 3/2002 | Jayaraman | |
| 6,406,420 B1 | 6/2002 | McCarthy et al. | |
| 6,416,510 B1 | 7/2002 | Altman et al. | |
| 6,425,918 B1 | 7/2002 | Shapiro et al. | |
| 6,447,443 B1 | 9/2002 | Keogh et al. | |
| 6,493,591 B1 | 12/2002 | Stokes | |
| 6,494,825 B1 | 12/2002 | Talpade | |
| 6,511,413 B2 | 1/2003 | Landesberg | |
| 6,566,406 B1 | 5/2003 | Pathak et al. | |
| 6,689,103 B1 | 2/2004 | Palasis | |
| 6,702,777 B2 | 3/2004 | Haim et al. | |
| 6,730,016 B1 | 5/2004 | Cox et al. | |
| 6,808,488 B2 | 10/2004 | Mortier et al. | |
| 6,887,974 B2 | 5/2005 | Pathak | |
| 6,908,424 B2 | 6/2005 | Mortier et al. | |
| 7,031,775 B2 | 4/2006 | Soykan et al. | |
| 7,044,905 B2 | 5/2006 | Vidlund et al. | |
| 7,094,230 B2 | 8/2006 | Flaherty et al. | |
| 7,103,418 B2 | 9/2006 | Laske et al. | |
| 7,104,988 B2 | 9/2006 | Altman et al. | |
| 7,189,199 B2 | 3/2007 | McCarthy et al. | |
| 7,731,649 B2 | 6/2010 | Ferrazzi | |
| 2002/0042554 A1 | 4/2002 | Alferness et al. | |
| 2002/0056461 A1 | 5/2002 | Jayaraman | |
| 2002/0077687 A1 | 6/2002 | Ahn | |
| 2002/0082469 A1 | 6/2002 | Taheri | |
| 2002/0106793 A1 | 8/2002 | West et al. | |
| 2002/0169360 A1 | 11/2002 | Taylor et al. | |
| 2002/0177772 A1 | 11/2002 | Altman et al. | |
| 2002/0188170 A1 | 12/2002 | Santamore et al. | |
| 2003/0060415 A1 | 3/2003 | Hung | |
| 2003/0078190 A1 | 4/2003 | Weinberg | |
| 2003/0078671 A1 | 4/2003 | Lesniak et al. | |
| 2003/0104568 A1 | 6/2003 | Lee | |
| 2003/0119718 A1 | 6/2003 | Wolff et al. | |
| 2003/0211793 A1 | 11/2003 | Bell et al. | |
| 2004/0002626 A1 | 1/2004 | Feld et al. | |
| 2004/0005295 A1 | 1/2004 | Lee et al. | |
| 2004/0010231 A1 | 1/2004 | Leonhardt et al. | |
| 2004/0023842 A1 | 2/2004 | Pathak et al. | |
| 2004/0102759 A1 | 5/2004 | Altman et al. | |
| 2004/0133063 A1 | 7/2004 | McCarthy et al. | |
| 2004/0158123 A1 | 8/2004 | Jayaraman | |
| 2004/0180043 A1 | 9/2004 | Sabbah et al. | |
| 2004/0208845 A1 | 10/2004 | Michal et al. | |
| 2004/0214760 A1 | 10/2004 | Gupta et al. | |
| 2004/0267083 A1 | 12/2004 | McCarthy et al. | |
| 2005/0003010 A1 | 1/2005 | Cohen et al. | |
| 2005/0004428 A1 | 1/2005 | Cox et al. | |
| 2005/0008628 A1 | 1/2005 | Feld et al. | |
| 2005/0065396 A1 | 3/2005 | Mortier et al. | |
| 2005/0080402 A1 | 4/2005 | Santamore et al. | |
| 2005/0131277 A1 | 6/2005 | Schweich, Jr. et al. | |
| 2005/0143620 A1 | 6/2005 | Mortier et al. | |
| 2005/0271631 A1 | 12/2005 | Lee et al. | |
| 2006/0002898 A1 | 1/2006 | Lee et al. | |
| 2006/0041243 A1 | 2/2006 | Nayak et al. | |
| 2006/0083717 A1 | 4/2006 | Lee et al. | |
| 2006/0083721 A1 | 4/2006 | Cohen et al. | |
| 2006/0111361 A1 | 5/2006 | Blackburn et al. | |
| 2006/0149123 A1 | 7/2006 | Vidlund et al. | |
| 2006/0233850 A1 | 10/2006 | Michal | |
| 2006/0241334 A1 | 10/2006 | Dubi et al. | |
| 2006/0253068 A1 | 11/2006 | van Bilsen et al. | |
| 2006/0276683 A1 | 12/2006 | Feld et al. | |
| 2007/0014784 A1 | 1/2007 | Nayak et al. | |
| 2007/0027487 A1 | 2/2007 | Mika et al. | |
| 2007/0042016 A1 | 2/2007 | Nayak et al. | |
| 2007/0093748 A1 | 4/2007 | Nayak et al. | |
| 2007/0112244 A1 | 5/2007 | McCarthy et al. | |
| 2007/0172472 A1 | 7/2007 | Nayak | |
| 2007/0233219 A1 | 10/2007 | Shafi et al. | |
| 2008/0065046 A1 | 3/2008 | Sabbah et al. | |
| 2008/0065047 A1 | 3/2008 | Sabbah et al. | |
| 2008/0069801 A1 | 3/2008 | Lee et al. | |
| 2008/0269720 A1 | 10/2008 | Sabbah | |
| 2009/0012413 A1 | 1/2009 | Sabbah et al. | |
| 2010/0030014 A1 | 2/2010 | Ferrazzi | |
| 2011/0087190 A1 | 4/2011 | Sabbah | |

FOREIGN PATENT DOCUMENTS

| | | |
|---|---|---|
| WO | 9948545 A1 | 9/1999 |
| WO | WO 01/07568 A2 | 2/2001 |
| WO | WO 01/10313 A1 | 2/2001 |
| WO | 02087481 A1 | 11/2002 |
| WO | 03043507 A2 | 5/2003 |
| WO | WO 03/080798 A2 | 10/2003 |
| WO | 03094855 A1 | 11/2003 |
| WO | 03095016 A1 | 11/2003 |
| WO | 2004050013 A2 | 6/2004 |
| WO | 2004091592 A2 | 10/2004 |
| WO | WO 2005/102181 A1 | 11/2005 |
| WO | 2007002554 A2 | 1/2007 |
| WO | WO 2007/024414 A2 | 3/2007 |

(56) References Cited

FOREIGN PATENT DOCUMENTS

| WO | WO 2007/024414 A3 | 3/2007 |
|---|---|---|
| WO | 2008030547 A1 | 3/2008 |

OTHER PUBLICATIONS

U.S. Appl. No. 60/813,184, Lee, et al.
U.S. Appl. No. 60/843,475, Lee, et al.
Kashem, Abul, et al., CardioClasp: A New Passive Device to Re-Shape Cardiac Enlargement, ASAIO Journal, 2002, pp. 1-7.
Kong, H., et al., Controlling Material Properties of Ionically Cross-linked Alginate Hydrogels by Varying Molecular Weight Distribution, Mat. Res. Soc. Symp. Proc., vol. 711, 2002, pp. GG5.7.1-GG5.7.4.
Lenfant, C., Cardiovascular Research: An NIH Perspective, Cardiovascular Surgery, vol. 5, No. 1, 1997, pp. 4-5.
Rastogi, Sharad, et al., Reversal of Maladaptive Gene Program in Left Ventricular Myocardium of Dogs With Heart Failure Following Long-Term Therapy with the Acorn Cardiac Support Device, Heart Failure Reviews, vol. 10, 2005, pp. 157-163.
Sabbah, Hani N., et al., Reversal of Chronic Molecular and Cellular Abnormalities Due to Heart Failure by Passive Mechanical Ventrical Containment, Circulation Research, vol. 93, 2003, pp. 1095-1101.
Torrent-Guasp, F., et al., Towards New Understanding of the Heart Structure and Function, European Journal of Cardio-thoracic Surgery, vol. 27, 2005, pp. 191-201.
Buckberg, Gerald D., Tenth RESTORE Group Meeting: Overview (Editorial), European Journal of Cardio-Thoracic Surgery, vol. 29, 2006, pp. S213-S-215.
Burkhoff, Daniel, New Heart Failure Therapy: The Shape of Things to Come? (Editorial), The Journal of Thoracic and Cardiovascular Surgery, vol. 125, No. 3, Mar. 2003, pp. S50-S52.
Cohn, Jay. N., et al., Report of the National Heart, Lung, and Blood Institute Special Emphasis Panel on Heart Failure Research, Circulation, vol. 95, 1997, pp. 766-770.
Christman, Karen L., et al., Fibrin Glue Alone and Skeletal Myoblasts in a Fibrin Scaffold Preserve Cardiac Function After Myocardial Infarction, Tissue Engineering, vol. 10, No. 3/4, 2004, pp. 403-409.
Christman, Karen L., et al., Injectable Fibrin Improves Cell Transplant Survival, Reduces Infarct Expansion, and Induces Neovasculature Formation in Ischemic Myocardium, Journal of American College of Cardiology, vol. 44, No. 3, Aug. 4, 2004, pp. 654-660.
Guccione, Julius M., et al., Myosplint Decreases Wall Stress Without Depressing Function in the Failing Heart: A Finite Element Model Study, The Annals of Thoracic Surgery, vol. 76, 2003, pp. 1171-1180.
Huang, Ngan F., Injectable Biopolymers Enhance Angiogenesis After Myocardial Infarction, Tissue Engeering, vol. 11, No. 11/12, 2005, pp. 1860-1866.
Kelley, Scott T., et al., Restraining Infarct Expansion Preserves Left Ventricular Geometry and Function After Acute Anteroapical Infarction, Circulation, vol. 99, 1999, pp. 135-142.
Kofidis, Theo, et al., Injectable Bioartificial Myocardial Tissue for Large-Scale Intramural Cell Transfer and Functional Recovery of Injured Heart Muscle, The Journal of Thoracic and Cardiovascular Surgery, vol. 128, No. 4, Oct. 2004, pp. 571-578.
Lenfant, Claude, Fixing the Failing Heart, Circulation, vol. 95, 1997, pp. 771-772.
Mann, Douglas L., Left Ventricular Size and Shape: Determinants of Mechanical Signal Transduction Pathways, Heart Failure Reviews, vol. 10, 2005, pp. 95-100.
McCarthy, Patrick M., et al., Device-Based Change in Left Ventricular Shape: A New Concept for the Treatment of Dilated Cardiomyopathy, The Journal of Thoracic and Cardiovascular Surgery, vol. 122, No. 3, Sep. 2001, pp. 482-490.
Ratacliffe, Mark B., Radio Frequency Heating of Chronic Ovine Infarct Leads to Sustained Infarct Area and Ventricular Volume Reduction, The Journal of Thoracic and Cardiovascular Surgery, vol. 119, No. 6, Jun. 2000, pp. 1194-1204.
Sabbah, Hani N., Global Left Ventricular Remodeling With the Acorn Cardiac Support Device: Hemodynamic and Angiographic Findings in Dogs With Heart Failure, Heart Failure Reviews, vol. 10, 2005, pp. 109-115.
Victal, Octavio A., et al., Left Ventricular Volume Reduction by Radiofrequency Heating of Chronic Myocardial Infarction in Patients With Congestive Heart Failure, Circulation, vol. 105, Mar. 19, 2002, pp. 1317-1322.
American Heart Association, 2001 Heart and Stroke Statistical Update, Dallas, Texas: American Heart Association, 2000.
Bioheart, Inc., Bioheart News, vol. 1, No. 2, 2000, 8 pages.
Gill, Robert M., et al., Cardiac Diastolic Dysfunction in Conscious Dogs With Heart Failure Induced by Chronic Coronary Microembolization, Am J. Physiol Heart Circ Physiol, vol. 291, Dec. 2006, pp. H3154-H3158.
Henry Ford Health System, Reply to Office Action, European Patent Application No. 08 742 708.4, dated Sep. 2, 2010, 5 pages.
Henry Ford Health System, Voluntary Amendment, European Patent Application No. 08 742 708.4, dated Dec. 7, 2009, 9 pages.
International Searching Authority / EPO, International Search Report, International Patent Application No. PCT/US2007/019496, dated Jan. 28, 2008, 6 pages.
International Searching Authority / EPO, International Search Report, International Patent Application No. PCT/US2007/019575, dated Feb. 16, 2009, 6 pages.
International Searching Authority / EPO, International Search Report, International Patent Application No. PCT/US2007/019581, dated Jan. 28, 2008, 6 pages.
International Searching Authority / EPO, International Search Report, International Patent Application No. PCT/US2008/004613, dated Aug. 25, 2009, 4 pages.
International Searching Authority / KIPO, International Search Report, International Patent Application No. PCT/US2008/007351, dated Jan. 13, 2009, 4 pages.
International Searching Authority / EPO, International Search Report, International Patent Application No. PCT/US2009/002269, dated Jun. 4, 2009, 6 pages.
International Searching Authority / EPO, Written Opinion of the International Searching Authority, International Patent Application No. PCT/US2007/019496, dated Jan. 28, 2008, 6 pages.
International Searching Authority / EPO, Written Opinion of the International Searching Authority, International Patent Application No. PCT/US2007/019575, dated Feb. 16, 2009, 6 pages.
International Searching Authority / EPO, Written Opinion of the International Searching Authority, International Patent Application No. PCT/US2007/019581, dated Jan. 28, 2008, 7 pages.
International Searching Authority / EPO, Written Opinion of the International Searching Authority, International Patent Application No. PCT/US2008/004613, dated Aug. 25, 2009, 8 pages.
International Searching Authority / KIPO, Written Opinion of the International Searching Authority, International Patent Application No. PCT/US2008/007351, dated Jan. 13, 2009, 6 pages.
International Searching Authority / EPO, Written Opinion of the International Searching Authority, International Patent Application No. PCT/US2009/002269, dated Jun. 4, 2009, 7 pages.
Kono, Tatsuji, et al., Left Atrial Contribution to Ventricular Filling During the Course of Evolving Heart Failure, Circulation, vol. 86, No. 4, Oct. 1992, pp. 1317-1322.
Landa, Natali, et al., Effect of Injectable Alginate Implant on Cardiac Remodeling and Function After Recent and Old Infarcts in Rat, Circulation, vol. 117, Mar. 2008, pp. 1388-1396.
Lee, Randall J., et al., Method and Apparatus for Using Biopolymer-Based Beads and Hydrogels for Cardiac Repair and Reconstruction and for Modification of Electrical Conduction in the Heart, U.S. Appl. No. 60/813,184, filed Jun. 13, 2006, 296 pages.
Lee, Randall J., et al., Intramyocardial Patterning for Cardiac Reshaping and Remodeling, U.S. Appl. No. 60/843,475, filed Sep. 8, 2006, 157 pages.

(56) References Cited

OTHER PUBLICATIONS

Sabbah, Hani N., The Cardiac Support Device and the Myosplint: Treating Heart Failure by Targeting Left Ventricular Size and Shape, Ann. Thorac Surg., vol. 75, 2003, S13-S19.
Sabbah, Hani N., Reply to Office Action, U.S. Appl. No. 12/082,368, dated Jun. 2, 2010, 18 pages.
Sabbah, Hani N., et al., Reply to Office Action U.S. Appl. No. 11/899,962, dated Apr. 13, 2009, 13 pages.
Sabbah, Hani N., et al., Request for Continued Examination, U.S. Appl. No. 11/899,962, dated Oct. 5, 2009, 24 pages.
Sabbah, Hani N., et al., Reply to Office Action U.S. Appl. No. 11/899,962, dated Jun. 22, 2010, 16 pages.
Sabbah, Hani N., et al., Request for Continued Examination, U.S. Appl. No. 11/899,962, dated Dec. 20, 2010, 18 pages.
Sabbah, Hani N., et al., Preliminary Amendment, U.S. Appl. No. 11/899,963, dated Jan. 7, 2008, 7 pages.
Sabbah, Hani N., et al., Reply to Office Action, U.S. Appl. No. 11/899,963, dated May 21, 2009, 23 pages.
Sabbah, Hani N., et al., Request for Continued Examination, U.S. Appl. No. 11/899,963, dated Feb. 19, 2010, 22 pages.
Symphony Medical, Inc., Article 19 Amendment, International Patent Application No. PCT/US2007/019496, dated Feb. 29, 2008, 7 pages.
Symphony Medical, Inc., Voluntary Amendment, European Patent Application No. 07 837 853.6, dated May 6, 2009, 7 pages.
U.S., Office Action, U.S. Appl. No. 11/899,962, dated Oct. 15, 2008, 28 pages.
U.S., Office Action, U.S. Appl. No. 11/899,962, dated Dec. 22, 2009, 37 pages.
U.S., Office Action, U.S. Appl. No. 11/899,962, dated Aug. 24, 2010, 35 pages.
U.S., Office Action, U.S. Appl. No. 12/082,368, dated Dec. 3, 2009, 15 pages.
Wall, Samuel T., et al., Theoretical Impact of the Injection of Material Into the Myocardium: A Finite Element Model Simulation, Circulation AHA 106.657270, 2006, pp. 1-9.
Henry Ford Health System, Voluntary Amendment, European Patent Application No. 09 730 816.7, dated Jan. 10, 2011, 7 pages.
Ferrazzi, Paolo, et al., Implantation of an Elastic Ring at Equator of the Left Ventricle Influences Cardiac Mechanics in Experimental Acute Ventricular Dysfunction, Journal of the American College of Cardiology, vol. 50, No. 18, 2007, pp. 1791-1798.
Ferrazzi, Paolo, et al., The Titan Can Help TITIN: From Micro to Macro Myocardial Elasticity, Journal of Cardiovascular Medicine, vol. 7, No. 3, 2006, pp. 153-158.
European Patent Office, Office Action, European Patent Application No. 07 837 853.6, dated Sep. 23, 2010, 5 pages.
European Patent Office, Office Action, European Patent Application No. 07 837 908.8, dated Sep. 23, 2010, 5 pages.
European Patent Office, Office Action, European Patent Application No. 07 837 913.8, dated Sep. 23, 2010, 5 pages.
Symphony Medical, Inc., Reply to Office Action, European Patent Application No. 07 837 908.8, dated Feb. 17, 2012, 6 pages.
U.S.; Office Action: U.S. Appl. No. 12/157,711, dated Nov. 10, 2011, 53 pages.
Japanese Patent Office, Office Action: Japanese Patent Application No. 2009-524718, dated Mar. 28, 2012, 3 pages.
Wenk, Jonathan F., et al., A Method for Automatically Optimizing Medical Devices for Treating Heart Failure: Designing Polymeric Injection Patterns, Journal of Biomechanical Engineering, vol. 131, Dec. 2009, 121011-1-121011-7.
Sabbah, Hani N., et al., Reply to Office Action: U.S. Appl. No. 12/157,711, dated May 9, 2012, 15 pages.
Japanese Patent Office, Office Action: Japanese Patent Application No. 2009-527418, dated Mar. 28, 2012, 3 pages.
Japanese Patent Office, Office Action (Translation): Japanese Patent Application No. 2009-527418, dated Mar. 28, 2012, 4 pages.
European Patent Office, Office Action: European Patent Application No. 07 837 908.8, dated May 27, 2011, 6 pages.
European Patent Office, Office Action: European Patent Application No. 08 742 708.4, dated Jul. 25, 2011, 6 pages.
Henry Ford Health System, Petition (in Japanese): Japanese Patent Application No. 2010-503052, dated Mar. 28, 2011, 1 page.
Henry Ford Health System, Voluntary Amendment (in Japanese, with English Language Translation): Japanese Patent Application No. 2010-503052, dated Mar. 28, 2011, 9 pages.
Symphony Medical, Inc., Reply to Office Action: European Patent Application No. 07 837 853.6, dated Mar. 22, 2011, 8 pages.
Symphony Medical, Inc., Reply to Office Action: European Patent Application No. 07 837 908.8, dated Mar. 16, 2011, 17 pages.
U.S., Office Action, U.S. Appl. No. 12/972,186, dated Feb. 28, 2012, 59 pages.
Japanese Patent Office, Office Action: Japanese Patent Application No. 2009-527418, dated Mar. 28, 2012, 7 pages.
Japanese Patent Office, Office Action: Japanese Patent Application No. 2009-527418, dated Nov. 20, 2012, 12 pages.
Japanese Patent Office, Office Action: Japanese Patent Application No. 2009-527435, dated Nov. 20, 2012, 12 pages.
Japanese Patent Office, Office Action: Japanese Patent Application No. 2010-503052, dated Nov. 28, 2012, 7 pages.
U.S., Office Action: U.S. Appl. No. 11/899,962, dated Mar. 27, 2013, 59 pages.
Australian Patent Office, Office Action: Australian Patent Application No. 2007292923, dated Jun. 27, 2012, 4 pages.
Australian Patent Office, Office Action: Australian Patent Application No. 2007293055, dated Jun. 22, 2012, 3 pages.
Australian Patent Office, Office Action: Australian Patent Application No. 2008239681, dated Aug. 27, 2012, 4 pages.
European Patent Office, Office Action: European Patent Application No. 07 837 908.8, dated Jan. 10, 2013, 5 pages.
European Patent Office, Summons to Attend Oral Proceedings Pursuant to Rule 115(1) EPC: European Patent Application Serial No. 08 742 708.4, dated Sep. 20, 2012, 28 pages.
Henry Ford Health System, Reply to Office Action: European Patent Application No. 08 742 708.4, dated Jan. 19, 2012, 5 pages.
Henry Ford Health System, Reply (with amended claims) to Summons to Attend Oral Proceedings: European Patent Application Serial No. 08 742 708.4, dated Jan. 11, 2013, 11 pages.
Sabbah, Hani, Reply to Office Action, U.S. Appl. No. 11/899,962, dated Jan. 12, 2013, 13 pages.
Sabbah, Hani, Reply to Office Action: U.S. Appl. No. 12/972,186, dated Aug. 28, 2012, 16 pages.
Symphony Medical, Inc., Reply to Office Action: European Patent Application No. 07 837 908.8, dated Feb. 17, 2012, 6 pages.
Symphony Medical, Inc., Reply to Office Action (Amended Claims): Japanese Patent Application No. 2009-527418, dated Jul. 30, 2012, 10 pages.
Symphony Medical, Inc., Reply to Office Action (Written Argument): Japanese Patent Application No. 2009-527418, dated Jul. 30, 2012, 16 pages.
U.S., Office Action: U.S. Appl. No. 11/899,962, dated Jul. 13, 2012, 99 pages.
U.S., Office Action, U.S. Appl. No. 12/157,711, dated Nov. 10, 2011, 53 pages.
U.S., Office Action, U.S. Appl. No. 12/157,711, dated Jul. 16, 2012, 29 pages.
Australian Patent Office. Office Action: Australian Patent Application No. 2013204863, dated May 9, 2013. 4 pages.
Cardiopolymers, Inc. et al. Reply to Office Action: Australian Patent Application No. 2007292923, dated Jun. 13, 2013. 16 pages.
Cardiopolymers, Inc. et al. Reply to Office Action: Australian Patent Application No. 2007293055, dated Jun. 13, 2013. 22 pages.
Symphony Medical, Inc. Reply to Office Action (Amended Claims): Japanese Patent Application No. 2009-527418, dated May 20, 2013. 10 pages.
Symphony Medical, Inc. Reply to Office Action (Written Argument): Japanese Patent Application No. 2009-527418, dated May 20, 2013. 29 pages.
Symphony Medical, Inc. Reply to Office Action (Amended Claims): Japanese Patent Application No. 2009-527435, dated May 20, 2013. 9 pages.

(56) References Cited

OTHER PUBLICATIONS

Symphony Medical, Inc. Reply to Office Action (Written Argument): Japanese Patent Application No. 2009-527435, dated May 20, 2013. 28 pages.

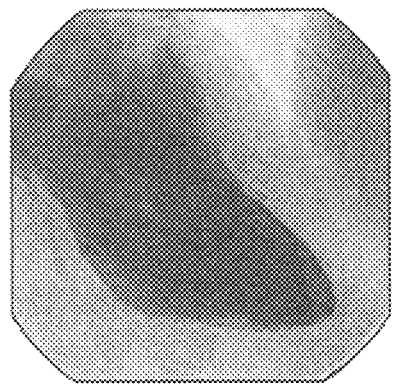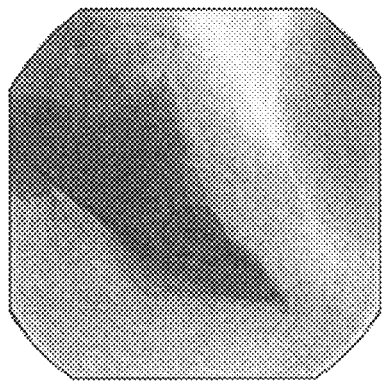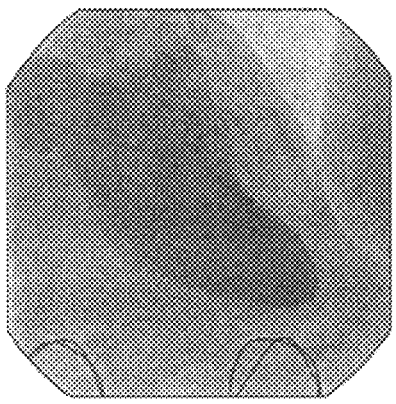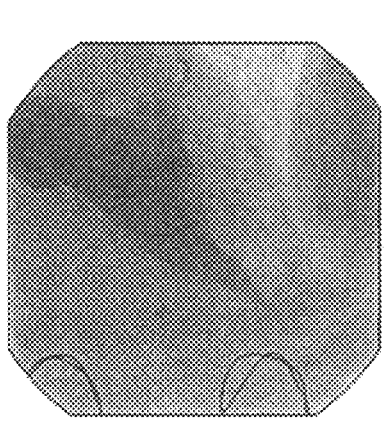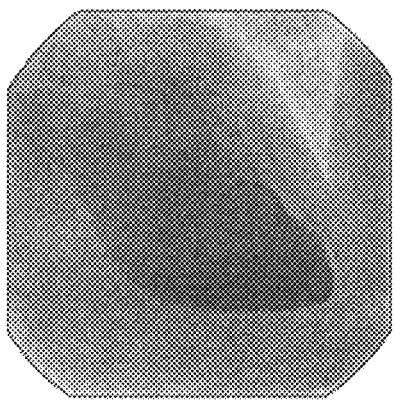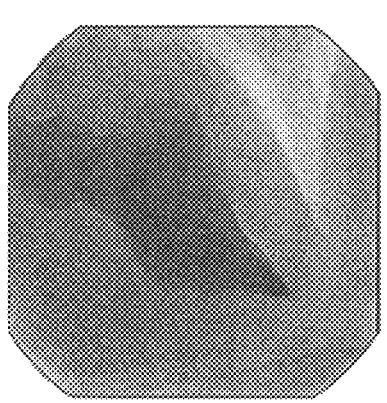
FIG. 18
FIG. 19

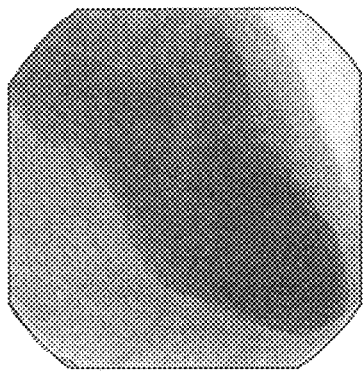 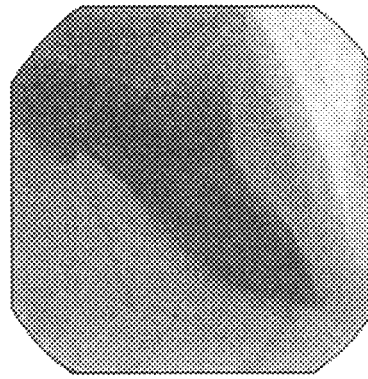
 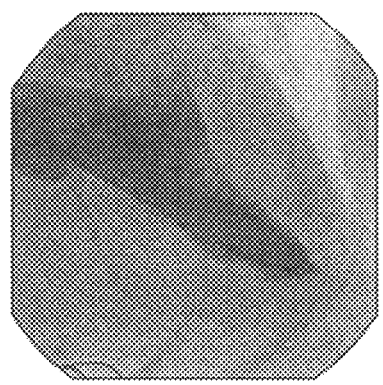
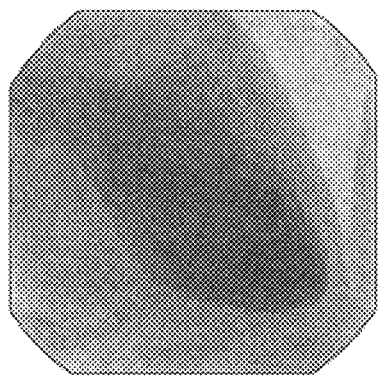 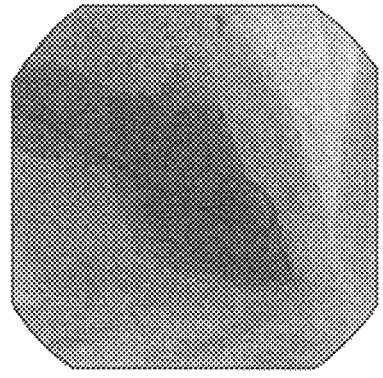
FIG. 20  FIG. 21

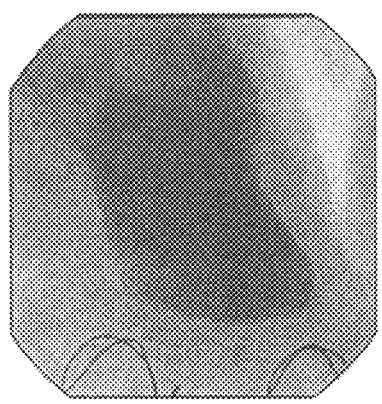
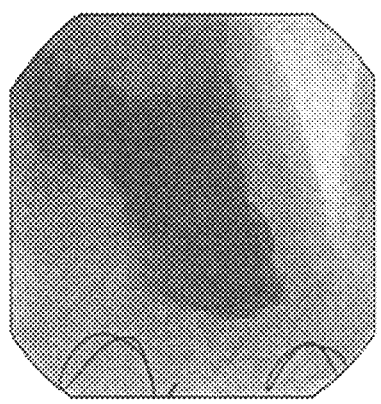
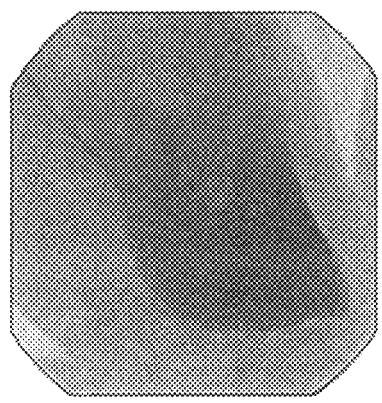
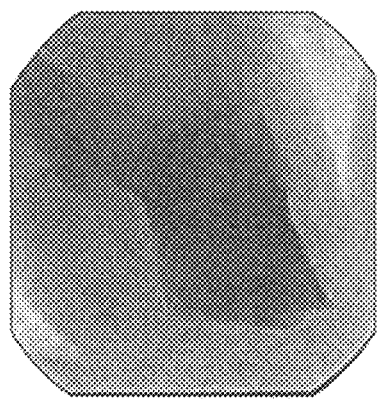
FIG. 22
FIG. 23

EDSI

| DOG# | Base | Pre | 2wks | 6wks |
|---|---|---|---|---|
| 07-039 | 1.70 | 1.60 | 2.00 | 2.00 |
| 07-052 | 1.80 | 1.70 | 2.00 | 2.00 |
| 06-114 | 1.60 | 1.40 | 1.50 | |
| | | | | |
| Mean | 1.70 | 1.57 | 1.83 | 2.00 |
| STD | 0.10 | 0.15 | 0.29 | 0.00 |
| SEM | 0.06 | 0.09 | 0.17 | 0.00 |

FIG. 24

ESSI

| DOG# | Base | Pre | 2wks | 6wks |
|---|---|---|---|---|
| 07-039 | 1.80 | 1.70 | 2.20 | 2.20 |
| 07-052 | 2.00 | 1.80 | 3.10 | 3.10 |
| 06-114 | 2.50 | 1.30 | 1.50 | |
| | | | | |
| Mean | 2.10 | 1.60 | 2.27 | 2.65 |
| STD | 0.36 | 0.26 | 0.80 | 0.64 |
| SEM | 0.21 | 0.15 | 0.46 | 0.45 |

FIG. 25

EDSI

| DOG# | Base | PRE | 2wks | 6wks | Post |
|---|---|---|---|---|---|
| 06-027 | 1.8 | 1.5 | 1.6 | 1.4 | 1.4 |
| 06-060 | 1.4 | 1.3 | 1.3 | 1.4 | 1.4 |
| 06-105 | 1.7 | 1.6 | 1.7 | 1.7 | 1.7 |
| 07-017 | 1.6 | 1.4 | 1.5 | 1.6 | 1.5 |
| 07-014 | 1.6 | 1.5 | 1.7 | 1.6 | 1.6 |
| 07-035 | 1.6 | 1.5 | 1.5 | 1.6 | 1.6 |
| Mean | 1.6 | 1.5 | 1.6 | 1.6 | 1.5 |
| STD | 0.1 | 0.1 | 0.2 | 0.1 | 0.1 |
| SEM | 0.1 | 0.0 | 0.1 | 0.1 | 0.0 |

FIG. 26

ESSI

| DOG# | Base | PRE | 2wks | 6wks | Post |
|---|---|---|---|---|---|
| 06-027 | 2.0 | 1.5 | 1.9 | 1.8 | 1.6 |
| 06-060 | 1.5 | 1.4 | 1.3 | 1.4 | 1.3 |
| 06-105 | 1.9 | 1.8 | 1.9 | 1.8 | 1.9 |
| 07-017 | 1.9 | 1.5 | 1.8 | 1.8 | 1.8 |
| 07-014 | 2.1 | 1.8 | 1.9 | 2 | 2.0 |
| 07-035 | 1.9 | 1.8 | 1.8 | 1.9 | 1.8 |
| Mean | 1.9 | 1.6 | 1.8 | 1.8 | 1.7 |
| STD | 0.2 | 0.2 | 0.2 | 0.2 | 0.3 |
| SEM | 0.1 | 0.1 | 0.1 | 0.1 | 0.1 |

FIG. 27

EDSI

| Dog # | Base | PRE | 2wks | 6wks | Post |
|---|---|---|---|---|---|
| 06-006 | 1.7 | 1.4 | 1.6 | N/A | 1.5 |
| 06-085 | 1.7 | 1.6 | 1.7 | 1.8 | 1.8 |
| 06-088 | 1.5 | 1.4 | 1.5 | 1.5 | 1.5 |
| Mean | 1.6 | 1.5 | 1.6 | 1.7 | 1.6 |
| STD | 0.1 | 0.1 | 0.1 | 0.2 | 0.2 |
| SEM | 0.1 | 0.1 | 0.1 | 0.2 | 0.1 |
|  |  |  |  |  |  |

FIG. 28

ESSI

| Dog # | Base | PRE | 2wks | 6wks | Post |
|---|---|---|---|---|---|
| 06-006 | 1.8 | 1.5 | 1.7 | N/A | 1.7 |
| 06-085 | 1.9 | 1.8 | 1.9 | 1.9 | 1.9 |
| 06-088 | 1.8 | 1.7 | 1.8 | 1.7 | 1.7 |
| Mean | 1.8 | 1.7 | 1.8 | 1.8 | 1.8 |
| STD | 0.1 | 0.2 | 0.1 | 0.1 | 0.1 |
| SEM | 0.0 | 0.1 | 0.1 | 0.1 | 0.1 |
|  |  |  |  |  |  |

FIG. 29

EDSI

| Dog # | Base | PRE | 2wks | 6wks | Post |
|---|---|---|---|---|---|
| 07-007 | 1.7 | 1.6 | 1.6 | 1.6 | 1.6 |
| 07-010 | 1.8 | 1.5 | 1.5 | 1.6 | 1.6 |
| 07-003 | 1.5 | 1.3 | 1.3 | 1.3 | 1.2 |
| 07-002 | 1.7 | 1.5 | 1.5 | 1.5 | 1.5 |
| 07-043 | 1.6 | 1.4 | 1.5 | 1.5 | |
| 07-028 | 1.7 | 1.5 | 1.6 | 1.5 | |
| | | | | | |
| | | | | | |
| Mean | 1.7 | 1.5 | 1.5 | 1.5 | 1.5 |
| STD | 0.1 | 0.1 | 0.1 | 0.1 | 0.2 |
| SEM | 0.0 | 0.0 | 0.0 | 0.0 | 0.1 |

FIG. 30

ESSI

| Dog # | Base | PRE | 2wks | 6wks | Post |
|---|---|---|---|---|---|
| 07-007 | 1.9 | 1.7 | 1.6 | 1.6 | 1.6 |
| 07-010 | 2.1 | 1.9 | 1.9 | 1.9 | 2 |
| 07-003 | 1.5 | 1.4 | 1.4 | 1.4 | 1.3 |
| 07-002 | 1.9 | 1.8 | 1.8 | 1.8 | 1.7 |
| 07-043 | 1.8 | 1.4 | 1.5 | 1.5 | |
| 07-028 | 2 | 1.9 | 1.9 | 1.9 | |
| | | | | | |
| Mean | 1.9 | 1.7 | 1.7 | 1.7 | 1.6 |
| STD | 0.2 | 0.2 | 0.2 | 0.2 | 0.3 |
| SEM | 0.1 | 0.1 | 0.1 | 0.1 | 0.1 |

FIG. 31

INTRAMYOCARDIAL PATTERNING FOR GLOBAL CARDIAC RESIZING AND RESHAPING

CROSS-REFERENCE TO RELATED APPLICATIONS

This application claims the benefit of U.S. Provisional Patent Application Ser. No. 60/843,475 filed Sep. 8, 2006, which hereby is incorporated herein in its entirety by reference thereto.

BACKGROUND OF THE INVENTION

Field of the Invention

The present invention relates to treatment of cardiac conditions in living beings, and more particularly to the use of intramyocardial patterning for global cardiac resizing and reshaping.

Description of Related Art

Cardiovascular disease ("CVD") is the leading cause of death in the United States; see, e.g., C. Lenfant, Fixing the Failing Heart, Circulation, Vol. 95, 1997, pages 771-772; American Heart Association, Heart and Stroke Statistical Update, 2001; C. Lenfant, Cardiovascular Research: An NIH Perspective, Cardiovasc. Surg., Vol. 5, 1997; pages 4-5; J. N. Cohn et al., Report of the National Heart, Lung, and Blood Institute Special Emphasis Panel on Heart Failure Research, Circulation, Vol. 95, 1997, pages 766-770.

Heart failure ("HF") is generally defined as a change in the pumping function of the heart accompanied by typical signs or symptoms. These symptoms typically include shortness of breath or fatigue. Heart failure is a syndrome of ventricular dysfunction in which both ventricles are usually involved to some extent. Left ventricular failure typically causes shortness of breath and fatigue, and right ventricular failure typically causes peripheral and abdominal fluid accumulation. Heart failure is a progressive disorder whereby the hemodynamic and symptomatic states of the patient worsen over time despite the absence of clinically apparent adverse events. The symptomatic deterioration is often accompanied by progressive left ventricular ("LV") chamber remodeling, a process characterized globally by changes in LV chamber size and shape and, at the cellular level, by ongoing loss of cardiomyocytes, myocyte hypertrophy and interstitial fibrosis. Myocyte loss, hypertrophy and accumulation of collagen in the interstitial compartment are important determinants of progressive LV dysfunction, while increased LV size and chamber sphericity are major determinants of functional mitral regurgitation (MR); a condition which depending on its severity can have a major impact on reducing LV stroke output which is already impaired in heart failure. Progressive LV dilation can also lead to LV wall stress and myocardial stretch. Increased LV wall stress leads to increased myocardial oxygen consumption, and myocardial stretch can activate stretch response proteins that may play an important role in the development of maladaptive cardiomyocyte hypertrophy. LV dilation and increased LV sphericity are also sensitive indicators of poor long-term outcome.

For these reasons, preventing or reversing remodeling has emerged as desirable in the treatment of cardiomyopathy. Cardiomyopathy is a general term for disease of heart muscle regardless of the underlying etiology, which may be, for example, ischemic, hypertensive, dilated, hypertrophic, infiltrative, restrictive, viral, postpartum, valvular, or idiopathic. Cardiomyopathy typically results in heart failure.

Examples of various types of cardiomyopathy are as follows. Cor pulmonale is right ventricular enlargement secondary to a lung disorder that produces pulmonary artery hypertension. Right ventricular failure may follow. Dilated congestive cardiomyopathy is myocardial dysfunction producing heart failure in which ventricular dilation and systolic dysfunction predominate. Hypertrophic cardiomyopathy is a congenital or acquired disorder characterized by marked ventricular hypertrophy with diastolic dysfunction but without increased afterload. Examples include valvular aortic stenosis, coarctation of the aorta, systemic hypertension). Restrictive cardiomyopathy is characterized by non-compliant ventricular walls that resist diastolic filling. Although the left ventricle is most commonly affected, both ventricles may be affected.

At the present time, the most effective treatment for patients in end-stage heart failure is heart transplantation. However, given the chronic shortage of donor hearts, alternate strategies are needed to improve the lives of those with heart failure. Moreover, transplantation is not the most suitable treatment option for patients with milder forms of the disease.

Another treatment approach involves the use of mechanical external constraints to limit, stop, or even reverse negative left ventricular remodeling. One previously disclosed study included suturing a polymeric mesh to the epicardial surface for the intended purpose of providing an external support to prevent LV dilation and deterioration of LV function post-MI. See Kelley S T, Malekan R, Gorman J H $3^{rd}$ et al., Restraining infarct expansion preserves left ventricle geometry and function after acute anteroapical infarction, Circulation 1999; 99:135-42. Another previously disclosed device that has been investigated provides a plurality of sutures that are implanted in an open-chest procedure across the ventricle under tension to provide a change in the ventricle shape and a decrease in chamber diameter. This trans-cavitary suture network is intended to decrease the radius of the ventricle to thus reduce ventricular wall stress. Another previously disclosed device under clinical investigation is generally a mesh structure that is implanted as a jacket around the heart and adjusted to provide a snug fit during open-chest surgery. It is intended that the jacket restrains the heart from further enlargement. See, for example, Hani N. Sabbah, Reversal of Chronic Molecular and Cellular Abnormalities Due to Heart Failure by Passive Mechanical Ventricular Containment, Circ. Res., Vol. 93, 2003, pages 1095-1101; Sharad Rastogi et al., Reversal of Maladaptive Gene Program in Left Ventricular Myocardium of Dogs with Heart Failure Following Long-Term Therapy with the Acorn Cardiac Support Devide, Heart Failure Reviews, Vol. 10, 2005, pages 157-163. Still another approach being investigated provides a nitinol mesh as a similar external restraining device to that described above; however, the super-elastic system is intended to assist in systolic contraction, and is generally intended for use via thoracoscopically guided minimally invasive delivery. Still another system being investigated includes a rigid ring that is implanted during open-chest surgery as another external constraining device to the ventricle. This ring is intended to decrease ventricular wall stress and prevent further enlargement of the heart by reducing the radius and modifying the shape of the ventricle. Examples of devices and methods similar to one or more of those discussed above have been disclosed by various companies, including the following: "Acorn;" "Myocor;" "Paracor;" "Cardioclasp;" and "Hearten." The Cardioclasp device is disclosed in an article by Abul Kashem et al., CardioClasp: A New Passive Device to Re-Shape Cardiac Enlargement, ASAIO Journal, 2002.

These prior techniques have had some success. Long term therapy with the Acorn Cardiac Support Device, for example, was reported to have halted progressive left ventricular dilation and to have improved ejection fraction. This improvement of global LV function was reported as being due to, at least in part, downregulation of stretch response proteins, attenuation of cardiomyocyte hypertrophy, and improvement of sarcoplasmic reticulum calcium cycling. Despite advances in the treatment of heart failure, further improvement in the speed of treatment and the complexity and intrusiveness of treatment techniques and devices is desirable.

Myocardial infarction ("MI") is a medical emergency in which some of the heart's blood supply is suddenly and severely reduced or cut off, causing the myocardium to die because it is deprived of its oxygen supply. A myocardial infarction may progressively advance into heart failure. Scar tissue formation and aneurysmal thinning of the infarct region often occur in patients who survive myocardial infarctions. It is believed that the death of cardiomyocytes results in negative left ventricular (LV) remodeling which leads to increased wall stress in the remaining viable myocardium. This process results in a sequence of molecular, cellular, and physiological responses which lead to LV dilation. Negative LV remodeling is generally considered an independent contributor to the progression of heart failure.

Mitral regurgitation ("MR") is incompetency of the mitral valve causing flow from the left ventricle (LV) into the left atrium during systole. Common causes include mitral valve prolapse, ischemic papillary muscle dysfunction, rheumatic fever, and annular dilation secondary to LV systolic dysfunction and dilation.

Despite advances in the treatment of aneurysmal thinning and mitral regurgitation, improved treatment techniques and devices are desirable, especially in conjunction with treatment of heart failure.

BRIEF SUMMARY OF THE INVENTION

One embodiment of the present invention is a method of treating a dilated chamber in a heart of a patient, comprising introducing a dose of biocompatible space-occupying agent into a plurality of sites within a myocardial wall of the chamber, the sites being disposed in a therapeutically effective pattern, and the dose being a therapeutically effective amount for thickening the myocardium, reducing systolic volume of the chamber, and improving function of the chamber.

Another embodiment of the present invention is a kit for treating a dilated chamber in a heart of a patient, comprising a source of biocompatible space-occupying agent; and means for introducing a dose of the biocompatible space-occupying agent into a plurality of sites within a myocardial wall of the chamber, the sites being disposed in a therapeutically effective pattern, and the dose being a therapeutically effective amount for thickening the myocardium, reducing systolic volume of the chamber, and improving function of the chamber.

Another embodiment of the present invention is a method of treating a heart having a myocardium, comprising establishing a pattern of intramyocardial supportive regions for globally treating a ventricle of the heart, the pattern comprising at least one ventricular line extending circumferentially about at least a portion of the ventricle; and introducing biocompatible material into myocardial tissue of the heart in accordance with the pattern to form the intramyocardial supportive regions.

Another embodiment of the present invention is a method of treating a heart having a myocardium, comprising establishing a pattern of intramyocardial supportive regions for globally treating a ventricle of the heart, the pattern comprising a plurality of elongated lines generally extending from near a base of the ventricle to near an apex of the ventricle; and introducing biocompatible material into myocardial tissue of the heart in accordance with the pattern to form the intramyocardial supportive regions.

Another embodiment of the present invention is a kit for treating a heart having a myocardium, comprising means for establishing a pattern of intramyocardial supportive regions for globally treating a ventricle of the heart, the pattern comprising at least one ventricular line extending circumferentially about at least a portion of the ventricle; and means for introducing biocompatible material into myocardial tissue of the heart in accordance with the pattern to form the intramyocardial supportive regions.

Another embodiment of the present invention is a kit for treating a heart having a myocardium, comprising means for establishing a pattern of intramyocardial supportive regions for globally treating a ventricle of the heart, the pattern comprising a plurality of elongated lines generally extending from near a base of the ventricle to near an apex of the ventricle; and means for introducing biocompatible material into myocardial tissue of the heart in accordance with the pattern to form the intramyocardial supportive regions.

BRIEF DESCRIPTION OF THE SEVERAL VIEWS OF THE DRAWINGS

FIGS. 18-23 are ventriculographs of hearts in end diastole and end systole over time, for animals in the pattern study.

FIGS. 24-31 are tables of sphericity index values for animals in the various studies.

DETAILED DESCRIPTION OF THE INVENTION, INCLUDING THE BEST MODE

As described herein, cardiomyopathy may be treated by distributing a space-occupying agent within the myocardium in a pattern about one or more chambers of the heart, such that the space-modifying agent integrates into and thickens at least part of the cardiac wall about the chamber so as globally to reduce wall stress and stabilize or even reduce chamber size. Some patterns also cause a beneficial global reshaping of the chamber. These changes occur quickly and are sustainable, and have a rapid and sustainable therapeutic effect on cardiac function. Over time the relief of wall stress reduces oxygen consumption and promotes healing. Moreover, various long-term therapeutic effects may be realized depending on the properties of the space-occupying agent, including combinations with other therapeutic materials. Specific cardiac conditions treatable by these systems and methods include, for example, dilated cardiomyopathy (with or without overt aneurismal formations), congestive heart failure, and ventricular arrhythmias.

Figure 1:
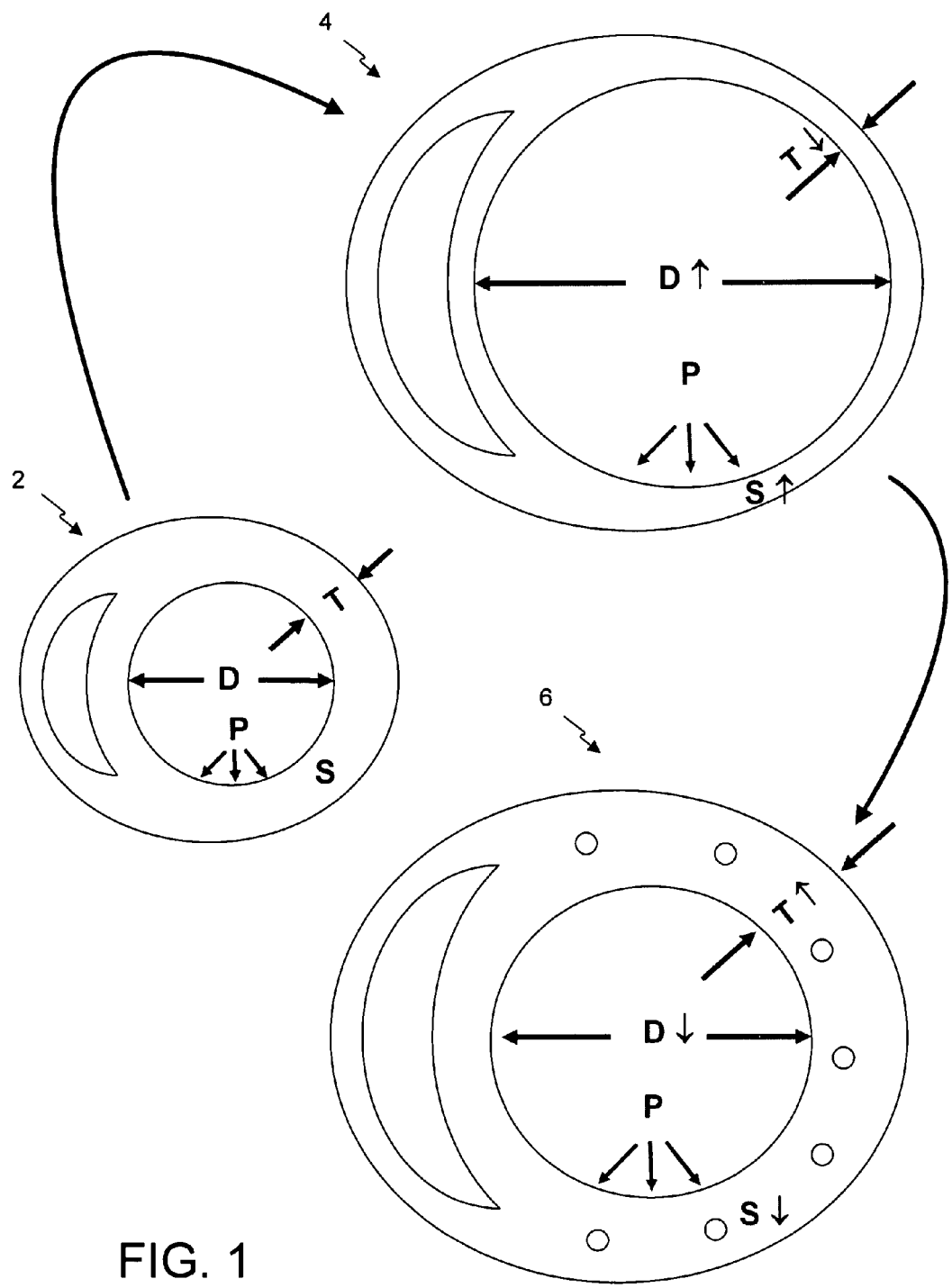
FIG. 1 is a schematic illustration of the mechanism of action for resizing a heart in heart failure, illustratively for the left ventricle.

FIG. 1 schematically illustrates the mechanism of action in a simplified manner, illustratively for the left ventricle. Wall stress "S" is an indicator of how hard the heart has to work to pump blood. Governed by the law of Laplace, wall stress is directed related to the diameter and wall thickness by the expression:

$$S=(D/T)P \quad (1)$$

where "D" is the chamber diameter, "T" is the thickness of the chamber wall, and "P" is pressure within the chamber. The heart in normal condition (reference number 2) has a left ventricle that is generally of an elongated conical shape (not shown in the plane of the drawing), which is an efficient shape for pumping. However, in heart failure patients the heart globally deteriorates to a condition (reference number 4) in which the diameter of the left ventricle gets bigger and the wall gets thinner. To achieve the same pressure P, the wall stress "S" goes up, meaning that the heart works harder. Moreover, the shape of the left ventricle (not shown in the plane of the drawing) changes from conical to spherical, which is not a efficient shape for pumping. Unfortunately, increased wall stress leads to a cascade of events which cause progressive remodeling. Remodeling stimuli resulting from increased wall stress includes cytokines, neurohormones, and oxidative stress. These remodeling stimuli cause ventricular enlargement due to myocyte hypertrophy and altered interstitial matrix, and systolic and diastolic dysfunction due to fetal gene expression, altered calcium-handling proteins, and myocyte death.

When space-occupying agent is distributed within the myocardium in a suitable pattern, the heart globally improves to a condition (reference number 6) in which the wall of the left ventricle thickens and the chamber diameter decreases. As thickness goes up and diameter goes down, the wall stress "S" is reduced. The cascade of events that result in progressive remodeling is interrupted, and progressive remodeling is halted or even reversed.

Figure 2:
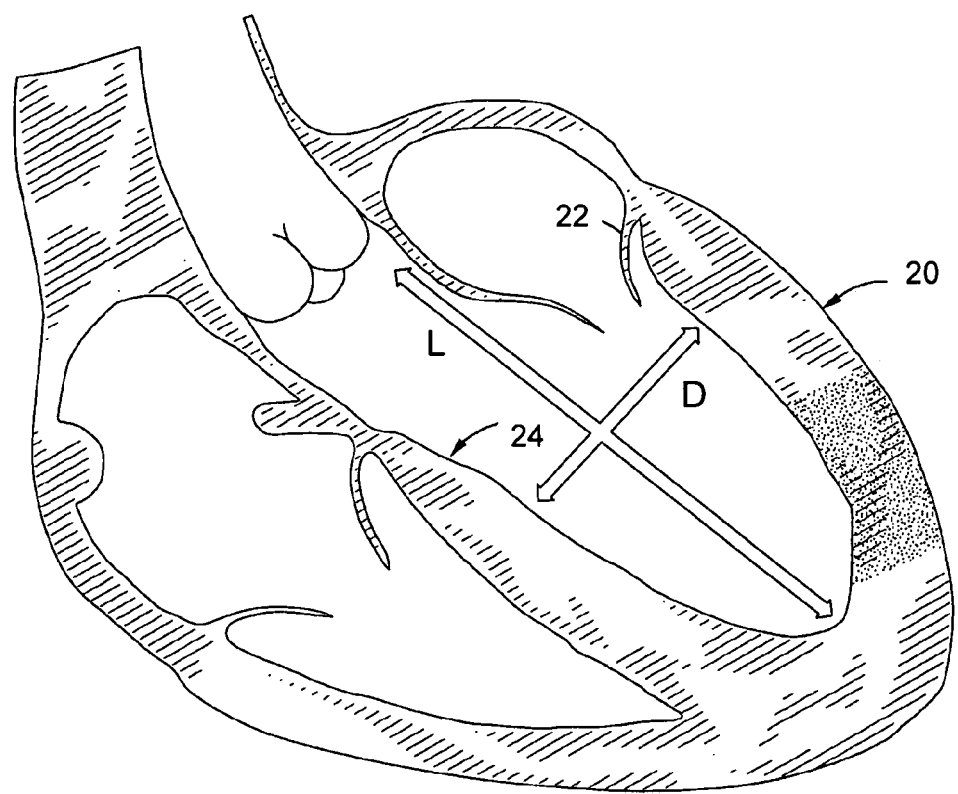
FIG. 2 is a cross-section drawing of a heart in which the long axis and short axis of the left ventricle are identified.

Some patterns also cause a beneficial reshaping of the chamber, effectively reversing LV remodeling for the treatment of heart failure. The shape of the left ventricle may be roughly quantified using, for example, the "end-systolic sphericity index," which as shown in FIG. 2, is the ratio of the long axis length "L" to the mid-cavity diameter "D," both measured at end systole. The normal cardiac sphericity index decreases as the shape of the left ventricle deviates from the ideal conical shape and approaches spherical. Reshaping to a more physiological ellipsoid shape, and in particular to a conical shape, is desirable.

Patterns of distribution of space-occupying agent within the myocardium for global resizing may also be used or augmented to treat localized conditions such as myocardial infarctions, overt aneurysm of the ventricular wall as typically forms in response to large transmural myocardial infarctions, and mitral regurgitation due to a noncompliant mitral valve. These techniques may also be used to treat localized conditions that may not yet have progressed to cardiomyopathy.

Patterns of Distribution of Space-Occupying Agent

For treatment having a global effect, the space-occupying agent is injected or implanted into the myocardium in patterns, which may be envisioned as shaped distributions of injection or implant sites (or both), or even more simply as one or more lines (including arcs) of injection or implant sites (or both). The pattern may be envisioned relative to the entire heart, to one or more ventricles of the heart, or to one or more atria of the heart to effect a global resizing and/or reshaping of the heart or one or more of its various chambers. In one suitable pattern, one or more lines may be envisioned that extend circumferentially about whole or part of one or more heart chambers such as the atria and ventricles. In the case of the left ventricle, for example, one or more such lines may be used, depending on the degree of enlargement of the left ventricle. The number of injection or implant sites per circumferential line depends on the size of the heart and location of the line, but may involve from, illustratively, two to eight sites, and preferably from five to seven sites. In another suitable pattern, lines may be envisioned that extend longitudinally the whole distance or part of the distance from proximate the apex to proximate the base. In the case of the left ventricle, for example, two or more such lines may be used, depending on the degree of enlargement of the left ventricle. The number of injection or implant sites per longitudinal line depends on the size of the heart and location of the line, but may involve from, illustratively, two to seven sites, and preferably from four to six sites. Where injections are used, the injections may be but need not necessarily be of uniform dose and spacing and depth within the myocardium. The injection sites may be in the middle of the myocardium, or closer to the endocardium or to the epicardium, as desired. Where implants are used, the implants may be but need not necessarily be of the same size and spacing and depth within the myocardium. The implant sites may be in the middle of the myocardium, or closer to the endocardium or to the epicardium, as desired. The contraction direction of the cardiac muscle fibers, which typically varies with depth in the myocardium, may be taken into account in deciding on the depth of the injection or implant.

The injectate or implants within the pattern may also be effective for treating conduction anomalies by modification of conduction in the myocardium, either by conduction block or by enhancing or attenuating conduction. The injections or implants are likely to disrupt conduction pathways, but this will not be pro-arrhythmic. To the extent that reentrant or other conduction anomalies are disrupted, the effect of a line of injection on cardiac electrical activity is beneficial. Conduction modification in the myocardium is disclosed in various documents, including US Patent Application Publication No. 2006/0083717 published Apr. 20, 2006 in the name of Lee et al., US Patent Application Publication No. 2006/0002898 published Jan. 5, 2006 in the name of Lee et al., US Patent Application Publication No. 2004/0005295 published Jan. 8, 2004 in the name of Lee et al., US Patent Application Publication No. 2003/0104568 published Jun. 5, 2003 in the name of Lee, and US Patent Application Publication No. 2005/0008628 published Jan. 13, 2005 in the name of Feld et al., all of which hereby are incorporated herein in their entirety by reference thereto.

Localized patterning may be used to treat a localized heart anomaly such as an aneurysm arising from a myocardial infract or a mitral valve annulus disorder resulting in mitral regurgitation, either on its own or as part of a global treatment. Mapping or imaging may be performed to identify the location of a localized heart anomaly, but is not necessary for the global treatment. Where used along with a global treatment, the local pattern may be envisioned separate from the generalized pattern, or integrated into the generalized pattern. Where injections are used, the injections may be but need not necessarily be of uniform dose and spacing and depth within the myocardium. The injection sites may be in the middle of the myocardium, or closer to the endocardium or to the epicardium, as desired. Where implants are used, the implants may be but need not necessarily be of the same size and spacing and depth within the myocardium. The implant sites may be in the middle of the myocardium, or closer to the endocardium or to the epicardium, as desired.

Figure 3A:
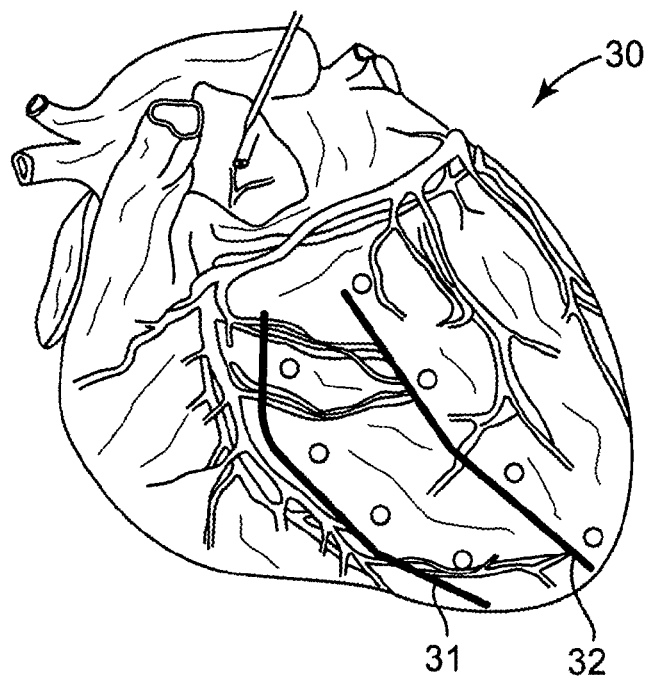
FIG. 3A is an anterior plan view of a heart on which a four longitudinal line pattern of injection sites is identified.
Figure 3B:
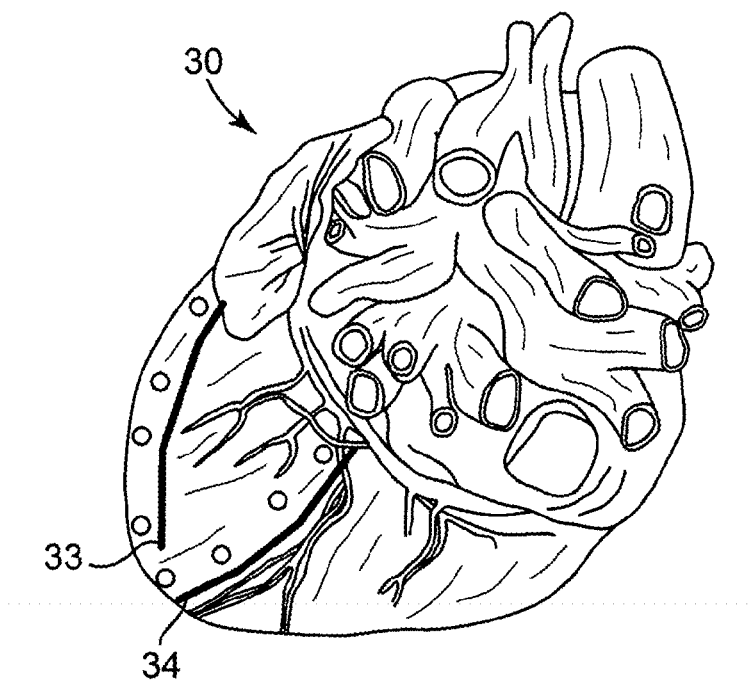
FIG. 3B is a posterior plan view of the heart of FIG. 3A.

FIG. 3A is an anterior plan view of heart 30, and FIG. 3B is a posterior view of heart 30. The injection sites in heart 30, the approximate locations of which are represented as white dots, may be envisioned as a pattern of four lines 31, 32, 33 and 34 that are spaced top to bottom and divided across the left ventricle free wall, which in this image runs from anterior and anterior lateral and around the back of this view to the posterior lateral surface of heart 30 shown in FIG. 3B. The distribution of the injections across the left ventricle free wall of heart 30 may be an even distribution, although in practice some deviation is likely due to limitations of the injection procedure, and the surgeon may in his discretion deviate from an even distribution. The lines, 31, 32, 33 and 34 are slightly spaced away from the injection sites so that the sites can be better identified on the heart 30.

Figure 4A:
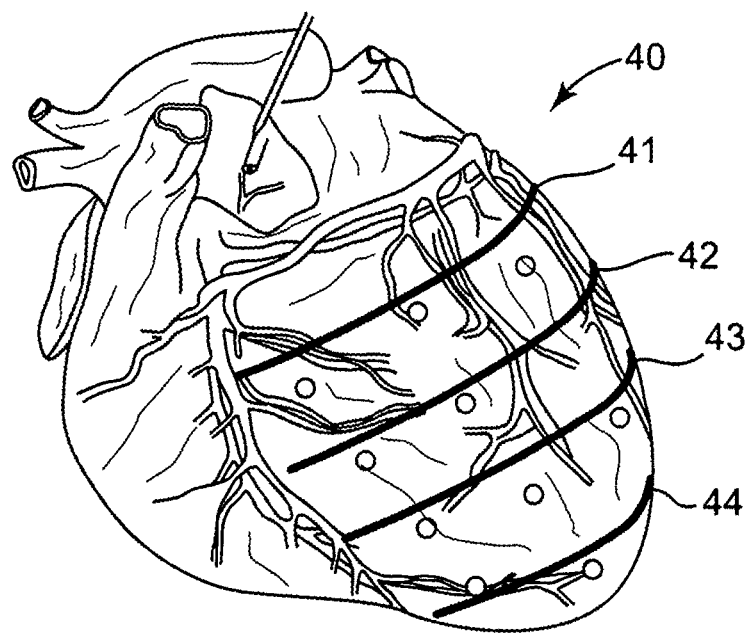
FIG. 4A is an anterior plan view of a heart on which a four circumferential line pattern of injection sites is identified.
Figure 4B:
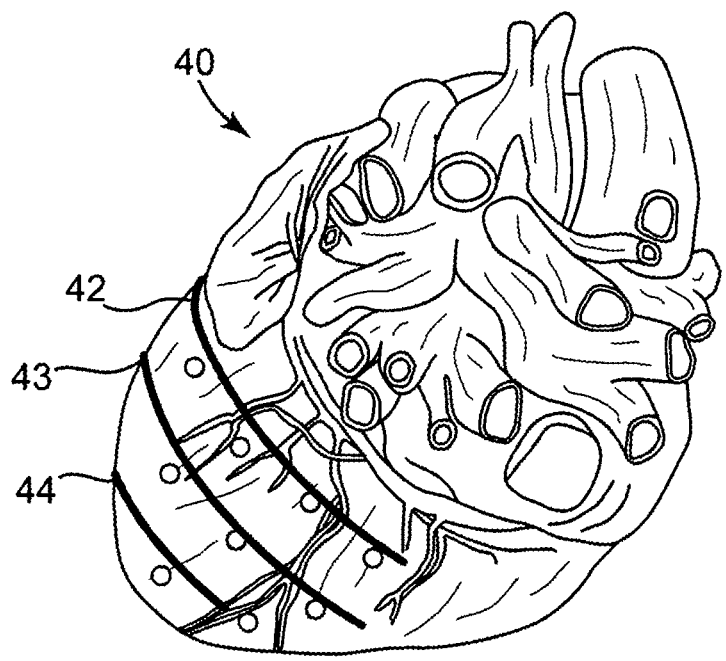
FIG. 4B is a posterior plan view of the heart of FIG. 4A.

FIG. 4A is an anterior plan view of heart 40, and FIG. 4B is a posterior view of heart 40. The injection sites in heart 40, the approximate locations of which are represented as white dots, may be envisioned as a pattern of four spaced-apart lines 41, 42, 43 and 44 which circumferentially span across most of the left ventricle free wall, which in this image runs from anterior and anterior lateral and around the back of this view to the posterior lateral surface of heart 40 shown in FIG. 4B. The distribution of the injections across the left ventricle free wall of heart 40 may be an even distribution, although in practice some deviation is likely due to limitations of the injection procedure, and the surgeon may in his discretion deviate from an even distribution. The lines 41, 42, 43 and 44 are slightly spaced away from the injection sites so that the sites can be better identified on the heart 40.

Figure 5A:
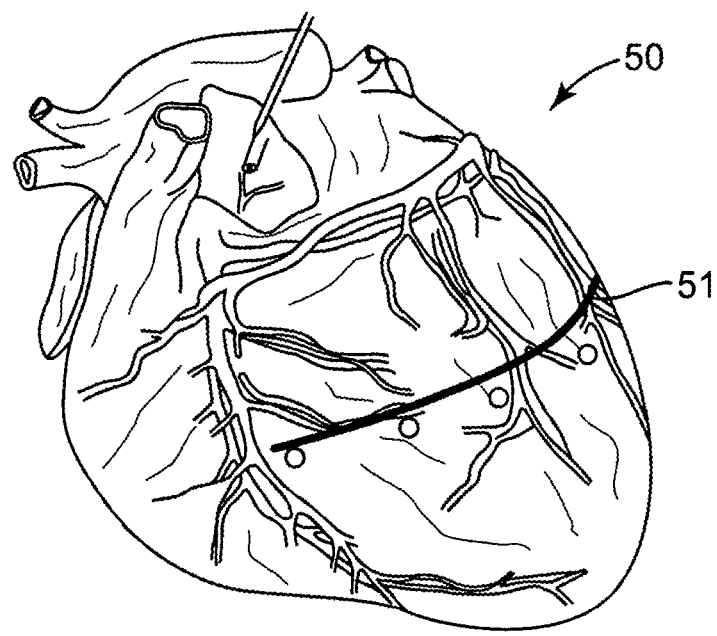
FIG. 5A is an anterior plan view of a heart on which a one circumferential line pattern of injection sites is identified.
Figure 5B:
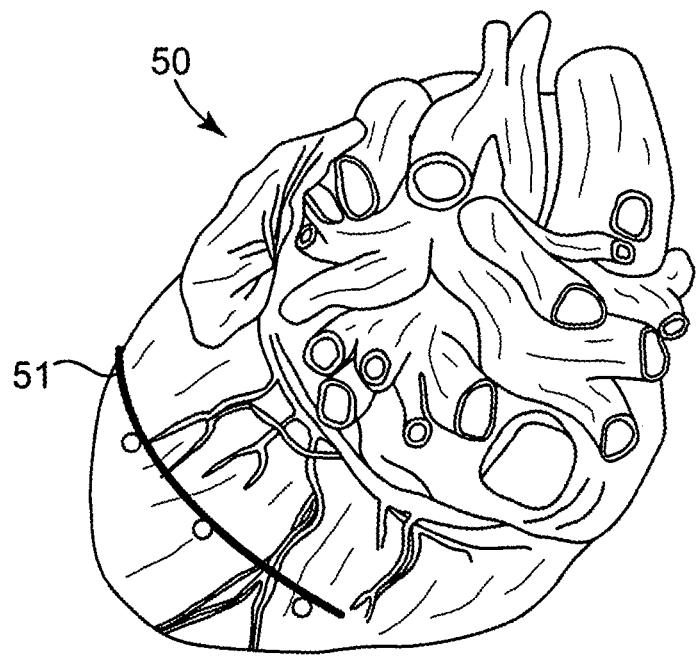
FIG. 5B is a posterior plan view of the heart of FIG. 5A.

FIG. 5A is an anterior plan view of heart 50, and FIG. 5B is a posterior view of heart 50. The injection sites in heart 50, the approximate locations of which are represented as white dots, may be envisioned as a pattern of one line 51 which circumferentially spans across most of the left ventricle free wall at the near widest part of the ventricle. In this image, the free wall runs from anterior and anterior lateral and around the back of this view to the posterior lateral surface of heart 50 shown in FIG. 5B. The distribution of the injections across the left ventricle free wall of heart 50 may be an even distribution, although in practice some deviation is likely due to limitations of the injection procedure, and the surgeon may in his discretion deviate from an even distribution. The line 51 is slightly spaced away from the injection sites so that the sites can be better identified on the heart 50.

Figure 6A:
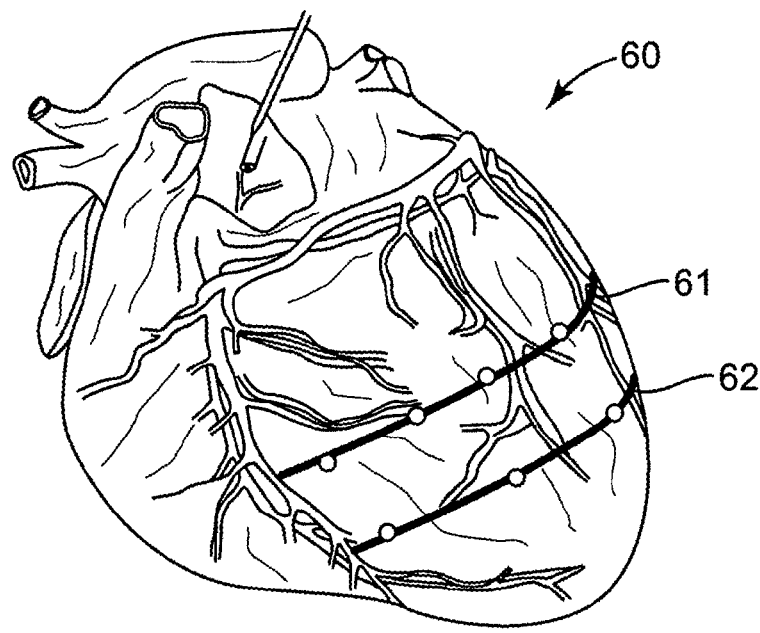
FIG. 6A is an anterior plan view of a heart on which a two circumferential line pattern of injection sites is identified.
Figure 6B:
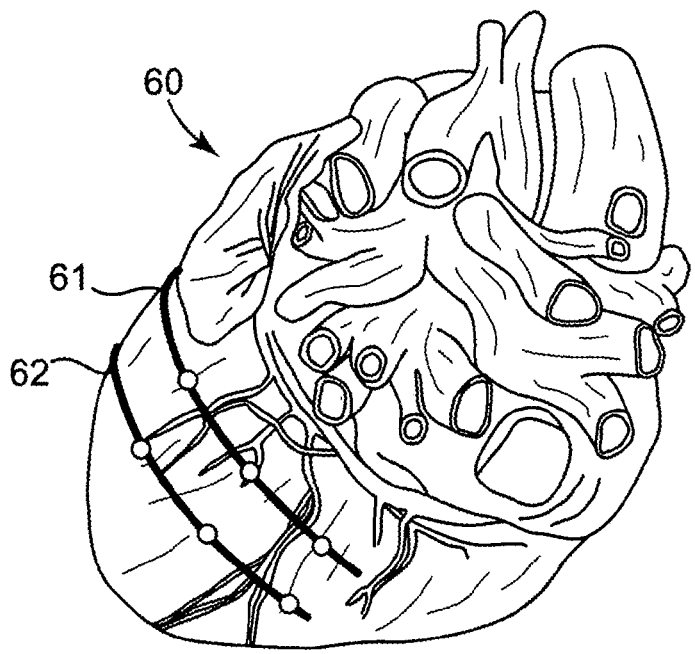
FIG. 6B is a posterior plan view of the heart of FIG. 6A.

FIG. 6A is an anterior plan view of heart 60, and FIG. 6B is a posterior view of heart 60. The injection sites in heart 60, the approximate locations of which are represented as white dots, may be envisioned as a pattern of two lines 61 and 62 which circumferentially span across most of the left ventricle free wall in proximity to the near widest part of the ventricle. The distribution of the injections across the left ventricle free wall of heart 60 may be an even distribution, although in practice some deviation is likely due to limitations of the injection procedure, and the surgeon may in his discretion deviate from an even distribution.

Figure 7A:
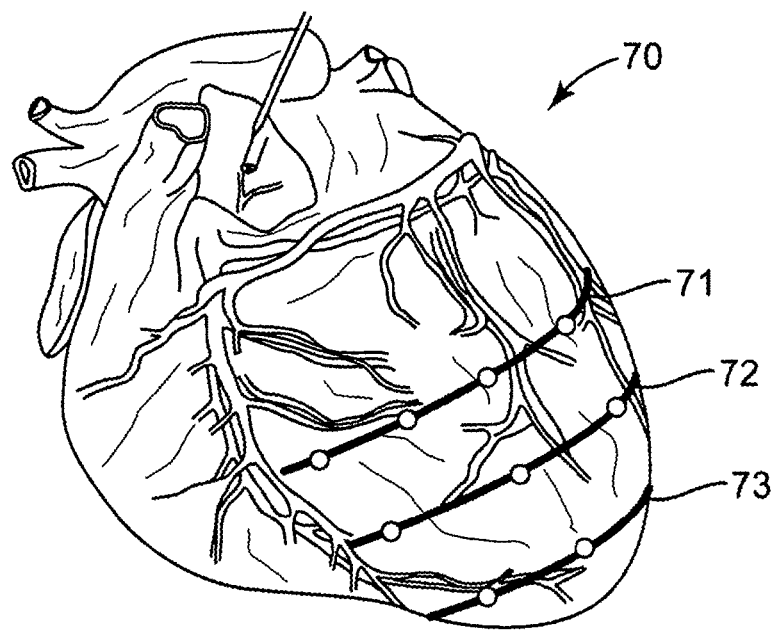
FIG. 7A is an anterior plan view of a heart on which a three circumferential line pattern of injection sites is identified.
Figure 7B:
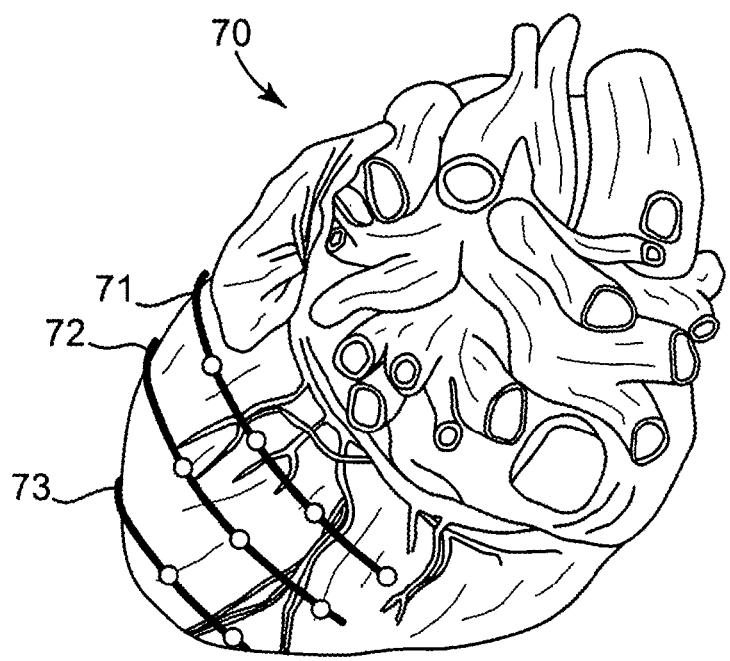
FIG. 7B is a posterior plan view of the heart of FIG. 7A.

FIG. 7A is an anterior plan view of heart 70, and FIG. 7B is a posterior view of heart 70. The injection sites in heart 70, the approximate locations of which are represented as white dots, may be envisioned as a pattern of three lines 71, 72 and 73, which circumferentially span across most of the left ventricle free wall. Line 71 may be in proximity to the near widest part of the ventricle, while lines 72 and 73 are spaced away toward the apex. Alternatively, lines 71 and 72 may both be in proximity to the near widest part of the ventricle, while line 73 is spaced away toward the apex. The distribution of the injections across the left ventricle free wall of heart 70 may be an even distribution, although in practice some deviation is likely due to limitations of the injection procedure, and the surgeon may in his discretion deviate from an even distribution.

Figure 8A:
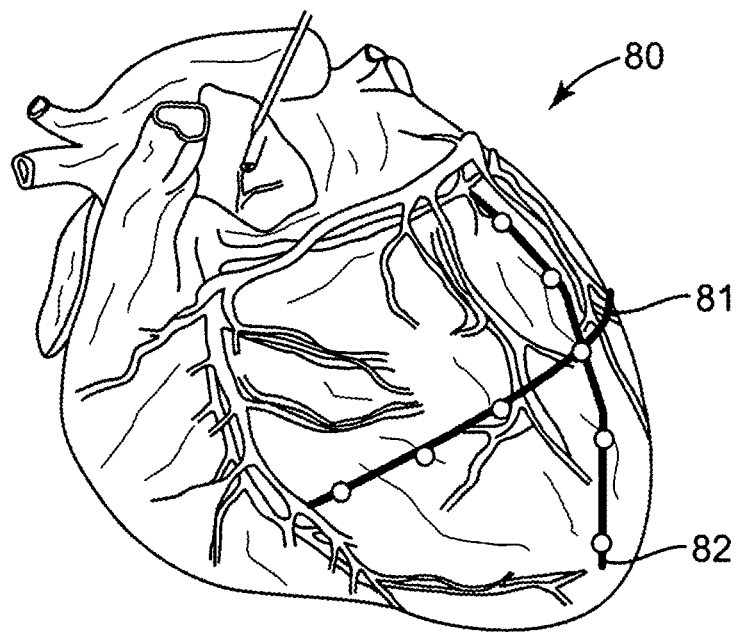
FIG. 8A is an anterior plan view of a heart on which a one circumferential line, one longitudinal line pattern of injection sites is identified.
Figure 8B:
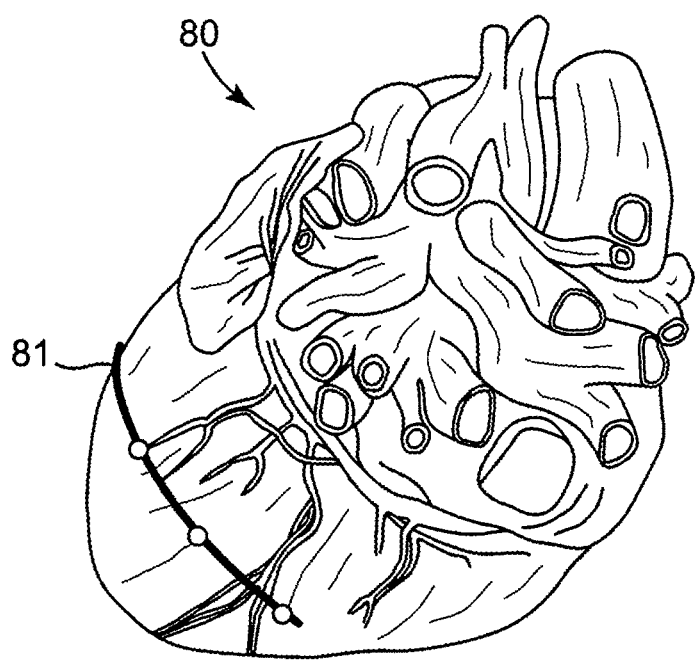
FIG. 8B is a posterior plan view of the heart of FIG. 8A.

FIG. 8A is an anterior plan view of heart 80, and FIG. 8B is a posterior view of heart 80. The injection sites in heart 80, the approximate locations of which are represented as white dots, may be envisioned as a pattern of one line 81 which circumferentially spans across most of the left ventricle free wall at the near widest part of the ventricle, and one line 82 that extends longitudinally the whole distance from proximate the apex to proximate the base. In this image, the free wall runs from anterior and anterior lateral and around the back of this view to the posterior lateral surface of heart 80 shown in FIG. 8B. The distribution of the injections across the left ventricle free wall of heart 80 may be an even distribution, although in practice some deviation is likely due to limitations of the injection procedure, and the surgeon may in his discretion deviate from an even distribution.

Intramyocardial patterning for global reshaping, global remodeling, or both global reshaping and remodeling is achieved with either injectable agents, implantable devices, or combinations thereof. The material for the injected or implanted pattern and the dose (for an injectable agent), size and configuration (for an implantable device), and other material properties such as, for example, stiffness, malleability, elasticity, water absorption, and so forth, is selected based on the intended therapeutic effect. Where an injectable agent is used, the dose may be uniform, or if desired may change (for example, may decrease toward the apex). Where implantable devices are used, devices of different cross-section may be used so that the effective cross-section may vary along the pattern. Where the therapeutic effect is primarily resizing and reshaping, a suitable material preferably provides prompt structural support and may dissipate over time. Alginate, chitosan, fibrin glue, collagen, PEG, and other such materials are illustrative of suitable materials for this purpose. Where long-term structural support is desired, the material preferably is resistant to absorption or breakdown by the body. Metals, polymers, silicone, and shaped memory materials are illustrative for this purpose. Where resizing, reshaping and reverse remodeling are desired, the material may be reabsorbed after providing some period of support and engineered so that it is replaced by myocytes, blood vessels, and so forth to provide the desired reverse remodeling. Injectable biopolymers in combination with cells such as fibroblasts, fibrocytes, stem cells, muscle cells, growth factors, stromal cell derived factor, or with other materials and/or cytokines that attract cells, or with both are suitable for this purpose. Materials useful for reshaping and/or remodeling include biologically-compatible polymers (including hydrogels, self-assembling peptides, PLGA, and any FDA approved polymer for human implantation), living cells (including, for example, fibroblasts, fibrocytes or profibrotic blood progenitor cells, stem cells, and muscle cells), growth factors (including, for example, angiogenic factors such as VEGF, FGF, and HGF; chemotractants: stem cell derived factor; and TGF-b), peptides, proteins, and mechanical devices made of metals, polymers (including plastics and silicone), shaped memory materials such as Nitonol, combinations of materials, and the like.

Where injectable agents are used, the individual injections may be spaced to have essentially no linkage with one another, the therapeutic effect being achieved initially through thickening of the myocardial wall due to the injection. Alternatively, the injections may be more closely spaced, with the dose of the individual injections being related to the spacing between the injections to achieve a mechanical, chemical, or both mechanical and chemical linkage between the injection sites, for realizing the therapeutic effect.

Injectors may be used to deliver injectable agents into cardiac structures so as to form therapeutic internal structures to promote cardiac reshaping, and implantable devices may be implanted so as to form therapeutic internal structures to promote cardiac reshaping. Many different types of injectors are known in the art, and one may select from them depending on the type of surgery (invasive or minimally invasive), the type of agent desired for use, and the pattern desired to be achieved by the injections. Suitable injectors include those described in U.S. Patent Application Publication 2005/0271631 published Dec. 8, 2005 in the name of Lee et al., which hereby is incorporated herein in its entirety by reference thereto. A multiple injection lumen array is disclosed in U.S. Pat. No. 6,689,103 issued Feb. 10, 2004 to Palasis, which hereby is incorporated herein in its entirety by reference thereto. Suitable injectors include injection catheters for minimally invasive procedures, and handheld syringes (single or multiple components with single or multiple lumen) for open chest procedures.

Pilot Study

A pilot study was undertaken to understand the effects of direct injections of alginate and fibrin sealant on the progression of left ventricular dysfunction and remodeling in dogs with heart failure. Six mongrel dogs received multiple sequential intracoronary embolizations with polystyrene latex microspheres 77-102 um in diameter, to achieve an LV ejection fraction equal to or less than thirty-five percent. Two weeks after the last embolization, three of the dogs received a patterned series of alginate injections and three of the dogs received a patterned series of fibrin sealant injections directly into the free myocardial wall of the left ventricle, generally within the mid-region, to determine whether the LV geometry could be sufficiently restored by reducing the end diastolic volume by approximately fifteen percent. The pattern of FIG. 3 was used, and each injection contained approximately 0.20 to 0.25 milliliters of either self-gelling alginate or of fibrin sealant. The alginate injectate was a self-gelling alginate formulation of Ca-Alginate/Na-Alginate available from the NovaMatrix Unit of FMC Biopolymer Corporation, 1735 Market Street, Philadelphia, Pa. 19103. The fibrin sealant injectate was a preparation using Evicel fibrin sealant (human) with transexamic acid added to the material. Evicel fibrin sealant is distributed by Johnson & Johnson of Somerville, N.J., USA. The results of the pilot study are described later, with reference to the bar graphs of FIG. 15, FIG. 16 and FIG. 17.

FIG. 3A shows an artistic rendition of the anterior view of a dog heart 30 highlighting the main anatomical features thereof. A clinical evaluation under standard IRB approval was undertaken to evaluate the feasibility of treating a beating dog heart with a pre-existing condition of an enlarged left ventricle. The animals under investigation presented an anterior bulge (dilation) in the left ventricle near the apex of the dog's heart. The surgical protocol was designed to inject biocompatible material via a hypodermic needle directly into myocardial tissue near, and possibly into, the dilated area.

Figure 9:
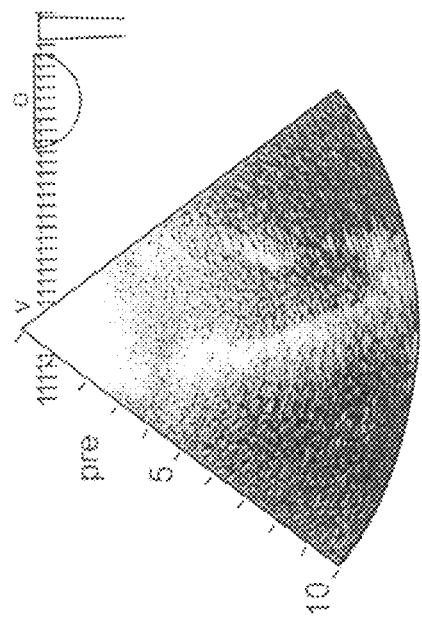
FIG. 9 is an ultrasonic transesophogeal echocardiograph showing the end-diastolic condition of a canine left ventricle prior to injection.
Figure 10:
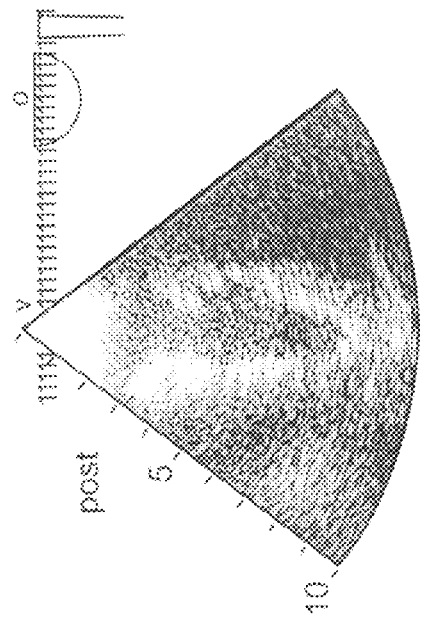
FIG. 10 is an ultrasonic transesophogeal echocardiograph showing the end-systolic condition of a canine left ventricle prior to injection.

Prior to surgical injection of the alginate solution, an ultrasonic transesophogeal echocardiograph was performed to characterize the extent and magnitude of the left ventricle dilation. The results of the pre-injection echocardiograph show a side view of the dog's left ventricle in which the extent of ventricular enlargement may be seen. FIG. 9 and FIG. 10 show respectively the end-diastolic condition and the end-systolic condition prior to alginate injection. A self-gelling alginate solution was prepared and then injected via an 18 gauge hypodermic needle into both the anterior and posterior regions of the dog's left ventricle region, in the pattern shown in FIG. 3A and FIG. 3B. In the present clinical evaluation, the alginate material was pre-mixed with a calcium cation ($Ca^{2+}$) prior to injection via the 18 gauge needle.

FIG. 3A shows the alginate injection locations in the anterior region of the dog's left ventricle as denoted by white circles. FIG. 3A shows 8 separate alginate injections, appearing geometrically as approximately two linear runs of 4 injections each running from the apex to the base region of the heart. In the present study, each injection contained approximately 0.20 to 0.25 milliliters of self-gelling alginate solution and the lateral separation of each injection ranged from approximately 10 to 15 millimeters. Similarly, FIG. 3B shows 8 separate alginate injections in the posterior region of the dog's left ventricle, and as before, approximately two linear runs of 4 injections each, wherein each injection contained approximately 0.20 to 0.25 milliliters of alginate solution and the lateral separation of each injection ranged from approximately 10 to 15 millimeters.

Figure 11:
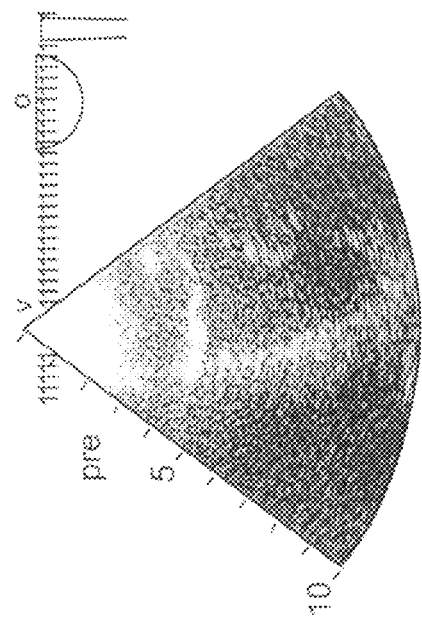
FIG. 11 is an ultrasonic transesophogeal echocardiograph showing the end-diastolic condition of a canine left ventricle after injection.
Figure 12:
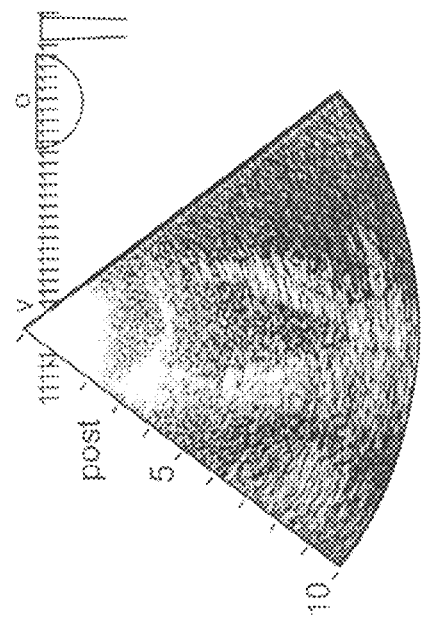
FIG. 12 is an ultrasonic transesophogeal echocardiograph showing the end-systolic condition of a canine left ventricle after injection.

Immediately following injection of the alginate solution into the dog's left ventricle region, a post injection transesophogeal echocardiograph was performed to characterize the effect of the alginate solution on the treated myocardial region. FIG. 11 and FIG. 12 depict respectively a side view of the dog's left ventricle region showing the end-diastolic and end-systolic condition immediately post alginate injection. As can be seen in FIG. 11 and FIG. 12, the dilated LV chamber responded to the treatment by forming a thicker chamber wall and more smoothly defined chamber.

Validation Study

A validation study was undertaken to test the hypothesis that direct injections of a biocompatible polymer, specifically alginate, to the left ventricle prevent the progression of left ventricular dysfunction and chamber remodeling in dogs with chronic heart failure. Twelve mongrel dogs received multiple sequential intracoronary embolizations with polystyrene latex microspheres 77-102 um in diameter, to achieve an LV ejection fraction equal to or less than thirty-five percent. Two weeks after the last embolization, six of the dogs received injections of alginate and six of the dogs (controls) received injections of saline directly into the free myocardial wall of the left ventricle, generally within the mid-region, using the pattern of FIG. 4. Each injection contained approximately 0.3 milliliters of either self-gelling alginate or saline. The results of the validation study are described later, with reference to the bar graphs of FIG. 15, FIG. 16 and FIG. 17.

Figure 13A:
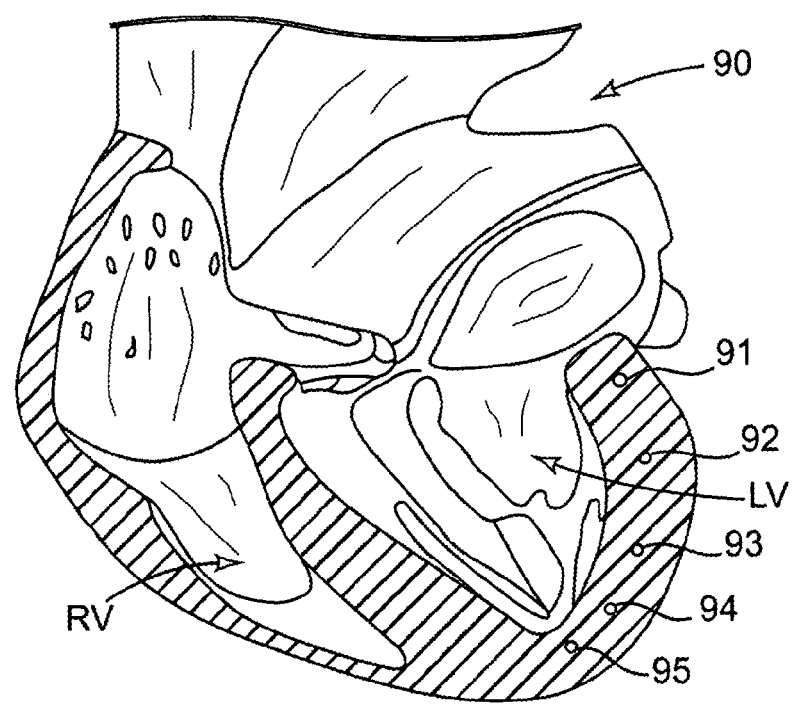
FIG. 13A is a long axis view and FIG. 13B is a short axis view of an illustrative dog heart with the sites of injection of alginate identified.
Figure 13B:
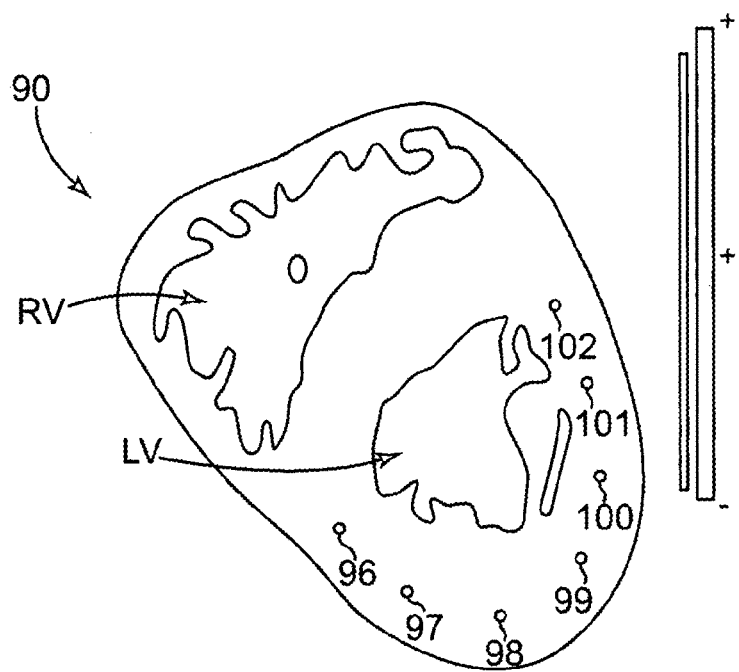

FIG. 13A is a long axis view and FIG. 13B is a short axis view of an illustrative dog heart 90 with the sites of injection of alginate identified. The pattern of FIG. 4 was used. In the long axis view (FIG. 13A), sites of injection 91-95 lie midway within the free wall of the left ventricle, along a longitudinal line from apex to base. In the short axis view, other sites of injection 96-102 lie midway within the free wall of the left ventricle, along a circumferential line.

Note that the short axis view of FIG. 13B shows the lack of placement of any injections into the septum. Injections and implants may be made into the septum if desired, and image guidance techniques well known to persons of ordinary skill in the art (e.g. echocardiography) may be used for septum injections and implants provided care is used to avoid injection of unintended targets such as the blood pool in the ventricles.

Although shown in the middle of the myocardium, the injection sites may be any depth within the myocardium, including closer to the endocardium or to the epicardium.

Pattern Study

A pattern study was undertaken to test the effect of a refined pattern of alginate injections, namely the pattern of FIG. 5, in preventing the progression of left ventricular dysfunction and chamber remodeling in dogs with chronic heart failure. Three mongrel dogs received multiple sequential intracoronary embolizations with polystyrene latex microspheres 77-102 um in diameter, to achieve an LV ejection fraction equal to or less than thirty-five percent. Two weeks after the last embolization, the dogs received injections of alginate directly into the free myocardial wall of the left ventricle, generally within the mid-region, using the pattern of FIG. 5. Each injection contained approximately 0.3 milliliters of self-gelling alginate. The results of the validation study are described later, with reference to the bar graphs of FIG. 15, FIG. 16 and FIG. 17.

Figure 14:
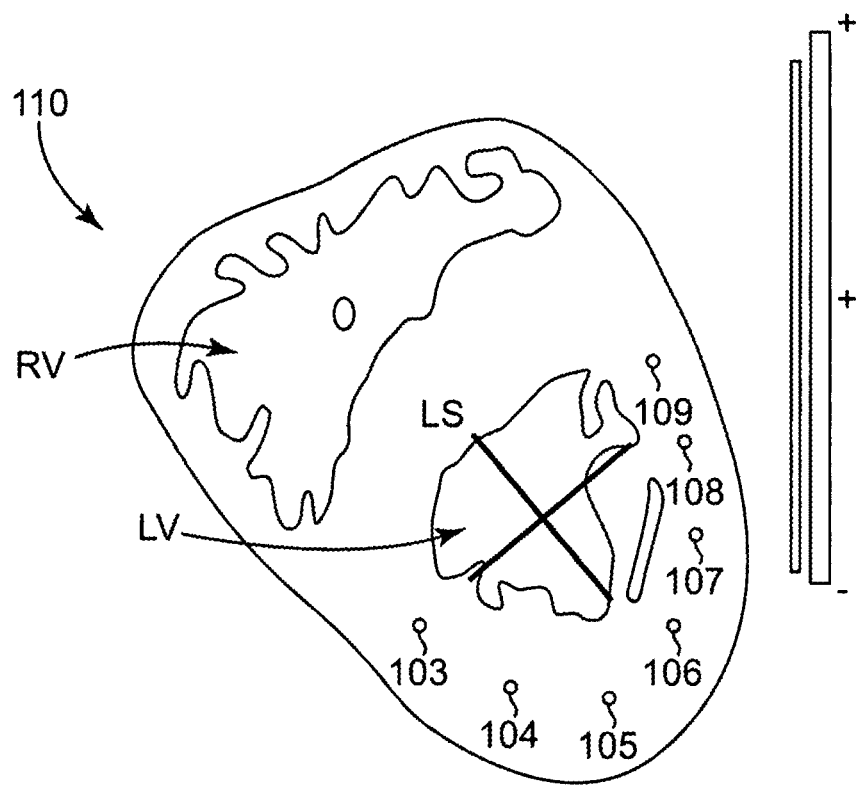
FIG. 14 is a short axis view of an illustrative dog heart in a plane near the widest point of the left ventricle, with the sites of injection of alginate identified.

FIG. 14 is a short axis view of an illustrative dog heart 110 in a plane near the widest point of the left ventricle, with the sites of injection of alginate identified. The pattern of FIG. 5 was used. In the short axis view, sites of injection 103-109 lie midway within the free wall of the left ventricle, along a circumferential line at the near widest part of the ventricle. The intent is to shrink the chamber at its widest point. The "lateral to septum" dimension is identified by "LS," and the "anterior to posterior" dimension is identified by AP.

Although shown in the middle of the myocardium, the injection sites may be any depth within the myocardium, including closer to the endocardium or to the epicardium.

Discussion of the Studies

The pilot, validation, and pattern studies were evaluated to determine if biocompatible polymers improve global left ventricle function and prevent progressive left ventricle chamber remodeling as assessed via changes in left ventricle end-systolic and end-diastolic volumes as well as changes in left ventricle chamber sphericity. On average for all animals, the baseline values of diastolic volume ("EDV"), end systolic volume ("ESV"), and ejection fraction ("EF") before HF embolism pretreatment and after HF embolism pretreatment in the pilot study were as shown in Table I below, in which the parenthetical value is the standard deviation.

TABLE 1

| Parameter | Baseline Value (Std. Dev.) | Pretreatment Value (Std. Dev.) |
|---|---|---|
| EDV | 51.53 ml (3.52) | 57.93 ml (4.7) |
| ESV | 24.6 ml (2.8) | 37.93 ml (2.02) |
| EF | 52.27% (5.51) | 34.2% (4.14) |

Figure 15:
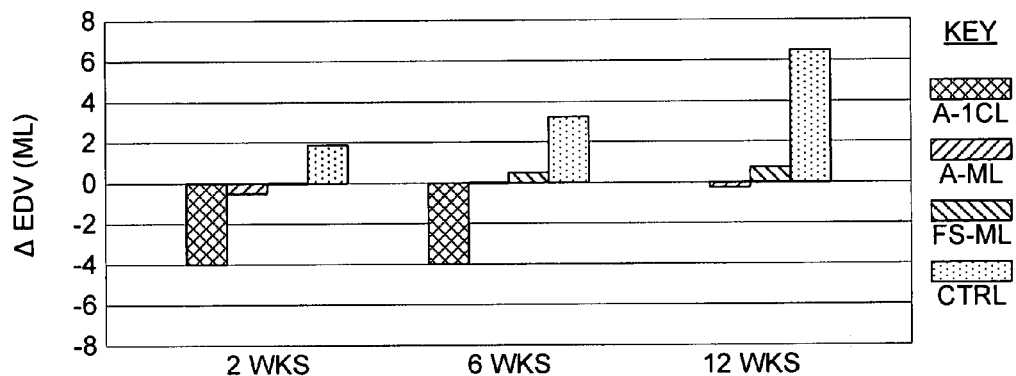
FIG. 15 is a graph showing changes in end diastolic volume (ΔEDV in milliliters) for animals in the various studies.
Figure 16:
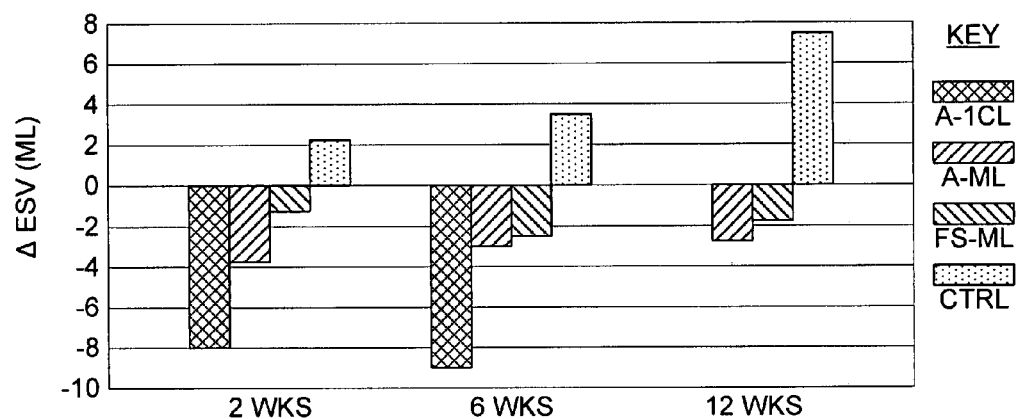
FIG. 16 is a graph showing changes in end systolic volume (ΔESV in milliliters) for animals in the various studies.
Figure 17:
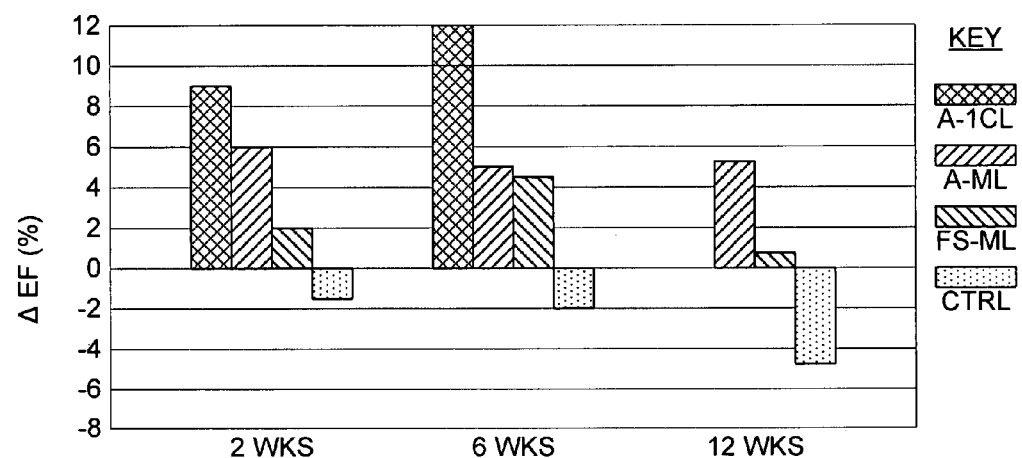
FIG. 17 is a graph showing changes in ejection fraction (ΔEF in percent) for animals in the various studies.

FIGS. 15, 16 and 17 respectively show changes in end diastolic volume ($\Delta$EDV in milliliters), in end systolic volume ($\Delta$ESV in milliliters), and in ejection fraction ($\Delta$EF in percent), for control animals injected in multiple line patterns ("CTRL") in the validation study, animals injected with fibrin sealant in multiple line patterns ("FS-ML") in the pilot study, animals injected with alginate in multiple line patterns ("A-ML") in the pilot and validation studies, and animals injected with alginate in a single circumferential line pattern ("A-1CL") in the pattern study. Twelve week data for the pattern study was not yet available. Changes in EDV relative to the pretreatment values are shown in Table 2 below.

TABLE 2

DELTA EDV

| Time Point | Alginate 1CL | Alginate ML | Fibrin Sealant ML | Control |
|---|---|---|---|---|
| 2 weeks | −4 | −0.5 (1.97) | 0 (1) | 1.83 (1.47) |
| 6 weeks | −4 | −0.017 (2.79) | 0.5 (2.12) | 3.33 (0.82) |
| 12 weeks | Not Available | −0.33 (3.33) | 0.67 (0.58) | 6.5 (1.91) |

Changes in ESV relative to the pretreatment values are shown in Table 3 below.

TABLE 3

DELTA ESV

| Time Point | Alginate 1CL | Alginate ML | Fibrin Sealant ML | Control |
|---|---|---|---|---|
| 2 weeks | −8 | −3.5 (2.43) | −1.33 (1.53) | 2.17 (1.83) |
| 6 weeks | −9 | −3 (1.9) | −2.5 (0.71) | 3.5 (1.64) |
| 12 weeks | Not Available | −2.83 (2.79) | −1.67 (1.53) | 7.5 (2.65) |

Changes in EF relative to the pretreatment values are shown in Table 4 below.

TABLE 4

DELTA EF

| Time Point | Alginate 1CL | Alginate ML | Fibrin Sealant ML | Control |
|---|---|---|---|---|
| 2 weeks | 9 | 6 (2.68) | 2 (3) | −1.5 (2.43) |
| 6 weeks | 12 | 5.17 (2.14) | 4.5 (0.71) | −2 (2.28) |
| 12 weeks | Not Available | 5.33 (3.2) | 0.67 (3.06) | −4.75 (2.87) |

The control animals show progressive deterioration in EDV, ESV and EF at the two week, six week, and twelve week intervals. End diastolic volume and end systolic volume in the control animals increased over time. This is the "normal" course for heart failure.

The animals treated with fibrin sealant using multiple line patterns showed some minor deterioration in EDV, sustained improvement in ESV, and short term improvement in EF. The EDV result nonetheless represented a significant retardation of the LV dilatation relative to the control animals, while the ESV result represented a significant retardation of the LV dilatation in systole relative to the control animals and also a slightly smaller chamber in systole.

The animals treated with alginate using multiple line patterns showed a small but noticeable and persistent reduction in EDV, a very noticeable and persistent improvement in ESV, and a good and persistent improvement in EF of around five percent. The disparity in systolic chamber size versus the modest improvement noted in diastole might be explained by improvement in LV mechanics and function. The theory of this intervention is that wall stress is reduced. Hence, a logical correlate might be that there is a more "forceful" contraction. This in turn may lead to a better contraction and small volumes in systole.

The animals treated with alginate using the single circumferential line pattern showed the greatest improvement, exhibiting substantial sustained improvement in EDV, substantial progressive improvement in ESV, substantial progressive improvement in EF, and significant reshaping of the chamber into a more desirable conical shape. The improvements are believed to result from the action of the single circumferential line injections, which essentially "cinch" the baggy globe shaped chamber back to a conical shape that is the most effective pump.

The improvements in are visible in the ventriculographs shown in FIGS. 18-23, and is quantified in the sphericity index values shown in the tables of FIGS. 24-31. Pretreatment, two week, and six week Vgraphs for dog 07-039 are shown in FIG. 18 for end diastole, and in FIG. 18 for end systole. Pretreatment, two week, and six week Vgraphs for dog 07-052 are shown in FIG. 20 for end diastole, and in FIG. 21 for end systole. Pretreatment and two week Vgraphs for dog 06-114 are shown in FIG. 22 for end diastole, and in FIG. 23 for end systole.

The shape improvement visible in FIGS. 18-23 for the single circumferential line pattern are quantified in the sphericity index tables of FIGS. 24-25. FIG. 24 shows the end diastolic sphericity index at base, pretreatment, two weeks, and six weeks for all three dogs, along with the mean, standard deviation, and standard error of the mean. All dogs exhibited significant improvement in EDSI relative to pretreatment, and the improvement was sustained through six weeks for the dogs with data. The mean pretreatment EDSI was 1.57, which improved to 2.00 after six weeks. FIG. 25 shows the end systolic sphericity index at base, pretreatment, two weeks, and six weeks for all three dogs, along with the mean, standard deviation, and standard error of the mean. All dogs exhibited significant improvement in ESSI relative to pretreatment, and the improvement was sustained through six weeks for the dogs with data. The mean pretreatment ESSI was 1.60, which improved to 2.65 after six weeks.

FIGS. 26 and 27 show sphericity index data for six alginate dogs in the pilot and validation studies. FIG. 26 shows the end diastolic sphericity index at base, pretreatment, two weeks, six weeks, and twelve week post period, along with the mean, standard deviation, and standard error of the mean. Generally, EDSI changed little relative to pretreatment. The mean pretreatment EDSI was 1.5, and the six week EDSI was also 1.5. FIG. 27 shows the end systolic sphericity index at base, pretreatment, two weeks, six weeks, and twelve week post period, along with the mean, standard deviation, and standard error of the mean. While some animals exhibited improvement, generally ESSI changed little relative to pretreatment. The mean pretreatment ESSI was 1.6, and the six week ESSI was 1.7.

Despite little improvement in the EDSI and ESSI results, the alginate dogs in the pilot and validation studies avoided any further deterioration in their end diastolic volume (see A-ML bars in FIG. 15), sustained a significant improvement in their end systolic volume (see A-ML bars in FIG. 16), and sustained a significant improvement in their ejection fraction (see A-ML bars in FIG. 17). Even without dramatic shape improvement, improvement of end systolic volume relative to end diastolic volume is believed to be a desirable outcome suggestive of a greater ventricular pumping capacity.

FIGS. 28 and 29 show sphericity index data for three fibrin sealant dogs in the pilot study. FIG. 28 shows the end diastolic sphericity index at base, pretreatment, two weeks, six weeks, and twelve week post period, along with the mean, standard deviation, and standard error of the mean.

While some animals exhibited improvement, generally EDSI changed little relative to pretreatment. The mean pretreatment EDSI was 1.5, and the six week EDSI was 1.6. FIG. 29 shows the end systolic sphericity index at base, pretreatment, two weeks, six weeks, and twelve week post period, along with the mean, standard deviation, and standard error of the mean. While some animals exhibited improvement, generally ESSI changed little relative to pretreatment. The mean pretreatment ESSI was 1.7, and the six week ESSI was 1.8.

Despite little improvement in the EDSI and ESSI results, the fibrin sealant dogs in the pilot and validation studies exhibited only very slight deterioration in their end diastolic volume (see FS-ML bars in FIG. 15), sustained a significant improvement in their end systolic volume (see FS-ML bars in FIG. 16), and exhibited varying improvement in their ejection fraction (see FS-ML bars in FIG. 17). Even without dramatic shape improvement, improvement of end systolic volume relative to end diastolic volume is believed to be a desirable outcome suggestive of a greater ventricular pumping capacity.

FIGS. 30 and 31 show sphericity index data for the control dogs in the validation study. FIG. 30 shows the end diastolic sphericity index at base, pretreatment, two weeks, six weeks, and twelve week post period, along with the mean, standard deviation, and standard error of the mean. Generally EDSI changed little relative to pretreatment. The mean pretreatment EDSI was 1.5, and the six week EDSI was 1.5. FIG. 31 shows the end systolic sphericity index at base, pretreatment, two weeks, six weeks, and twelve week post period, along with the mean, standard deviation, and standard error of the mean. Generally ESSI changed little relative to pretreatment. The mean pretreatment ESSI was 1.7, which deteriorated to 1.6 at the six week point.

Along with little improvement in the EDSI and ESSI results, the control dogs experienced progressive HF, as indicated by their deteriorating end diastolic volume (see CTRL bars in FIG. 15), deteriorating end systolic volume (see CTRL bars in FIG. 16), and deteriorating ejection fraction (see CTRL bars in FIG. 17).

Other Patterns for Global Resizing and Reshaping

While the studies have focused on the left ventricle, the techniques may be used on other chambers of the heart or even on the whole heart. The techniques may be used to reshape and/or remodel the atria, and in particular an enlarged left atrium, to aid in prevention of atrial fibrillation and other atria-related conditions.

Figure 32A:
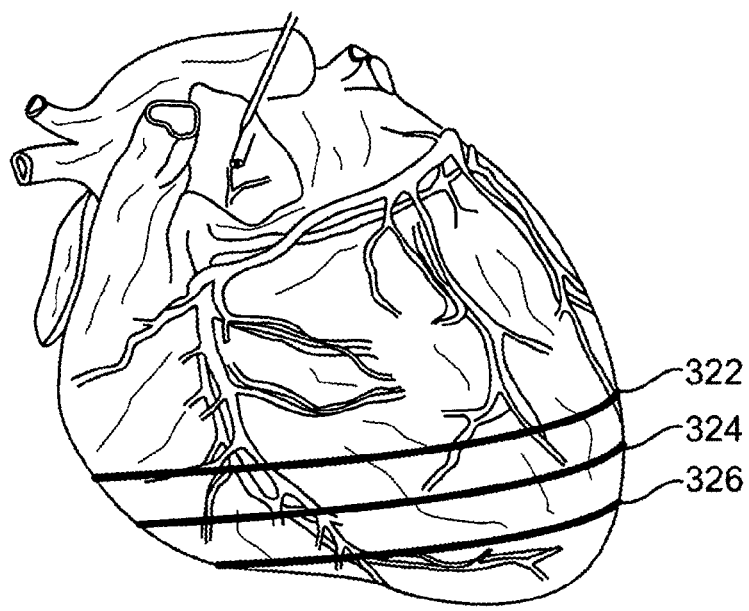
FIG. 32A is an anterior plan view of a heart on which a three circumferential line pattern of injection sites encompassing the entire lower portion of the heart is identified.
Figure 32B:
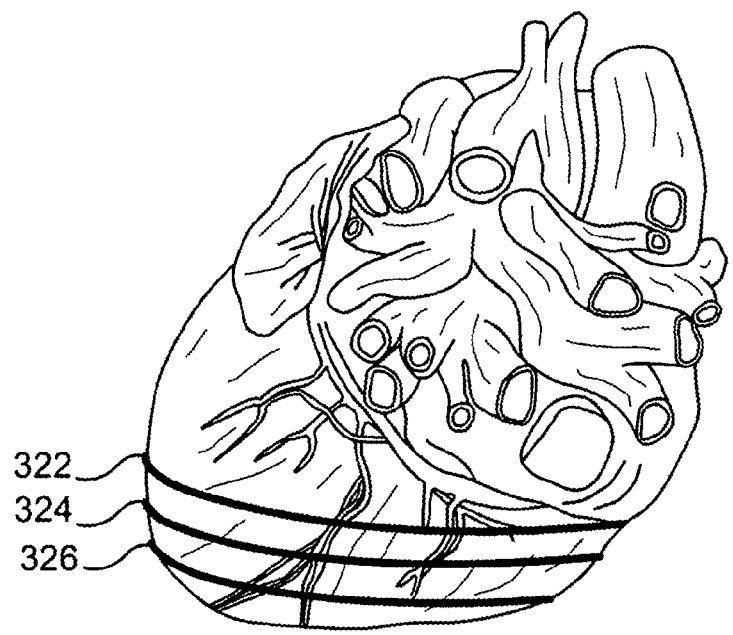
FIG. 32B is a posterior plan view of the heart of FIG. 32A.

The techniques may be used on the whole heart. FIGS. 32A and 32B show a treatment in which three circumferential lines 322, 324 and 326 are used to circumferentially encompass the entire lower portion of the heart, including the left and right ventricle.

Space-Occupying Agents

The clinical evaluation described above focused on the use of self-gelling alginate as the injectable biocompatible material into the dog's myocardial tissue. However, many different types of biocompatible materials, some injectable and some implantable, are suitable and may be used. For example, suitable injectable biocompatible materials may include: alginate beads, alginate material with covalently attached peptides, alginate beads coated with chitosan material, chitosan beads, fibrin glue, fibroblasts, fibrocytes, stem cells, growth factors, and combinations thereof. Biocompatible polymer materials of the type listed above are commercially available from numerous sources, including, for example, the NovaMatrix Unit of FMC Biopolymer Corporation, 1735 Market Street, Philadelphia, Pa. 19103, and Omrix Biopharmaceuticals, 630 $5^{th}$ Avenue, $22^{nd}$ Floor, New York, N.Y. 10111. Various materials are also described in U.S. Patent Application Publication 2005/0271631 published Dec. 8, 2005 in the name of Lee et al., which hereby is incorporated herein in its entirety by reference thereto. Other suitable materials include sugars such as monosaccharides, disaccharides, and trisaccharides.

Generally, biocompatible polymers are preferred for use as space-occupying agent principally for three reasons, namely (1) they provide immediately a physical structure or filler that thickens the heart wall and halts progression of remodeling, and in some cases reshapes and reverses remodeling; (2) they form matrices which for some polymers allows for in-situ tissue growth that promotes cell ingrowth for regeneration of functional tissue; and (3) administration is extremely flexible, ranging from minimally invasive techniques using catheters to open chest procedures.

Regarding the first reason, the structural property of the biopolymer leads to points of decreased wall stress in the damaged left ventricle which in turn produce beneficial cardiac mechanics in addition to decreases in chamber dimensions. The desired decrease in cardiac wall stress is influenced both by the volume of biopolymer administered and by the stiffness of the material itself. With respect to volume, we believe that increasing total wall volume more than an incidental amount, illustratively about 4.5% or more, produces a significant, beneficial change in volume/pressure. With respect to stiffness, we believe that a non-contractile material with equal or slightly higher stiffness than myocardium implanted into the myocardium will decrease wall stress (point fiber stress). For reference, normal myocardium displays a fiber stress of 1-10 kPa while infarcted and border zone myocardial tissue displays a fiber stress in the range of 20-30 kPa.

Regarding the second reason, matrices having a suitable porosity and constitution allow the in-growth of cardiomyocites from normal tissue into the infarcted zone of the wall, which can occur either spontaneously or through the application of chemokines, growth factors, or even cells into the area.

Desirable polymer properties for cardiac resizing and reshaping are as follows.

Origin/Purity. Ideally, the biopolymer is synthetic, fully-defined, and consistent. Human- or animal-sourced polymers such as fibrin sealants, bovine collagens, and so forth are suitable but may be at a regulatory and/or economic disadvantage.

Sterility. Suitable biopolymers are sterile and suitable for presentation to the operating room both in syringes (open surgical application) and in catheters (less invasive procedures).

Thrombogenicity. Suitable material is non-thrombogenic.

Immunogenicity. To realize a simple mechanic effect, inert, nonimmunogenic materials are preferable. However, materials containing bioreactive peptides or proteins such as growth factors to induce tissue ingrowth can be very beneficial.

Preparation. Minimal handling such as thawing and pre-mixing is desirable. The product preferably is pre-filled or loaded onto both syringes (open surgery) and catheter systems (less invasive).

Administration/Gel Time: The polymerization or gelling characteristics of the biopolymer is dependent on the number of lines and the number of injections per line. For patterns that involve on the order of 20 injections (doses), the time period may be around 20 minutes. For patterns such as the single circumferential line that may involve as few as two or three injections and preferably no more than seven or eight injections, the time period is considerably shorter. The polymer may be delivered as a single mass or as microspheres.

Hardness/Density. We believe that the polymer should preferably have properties (stress strain relation) that make it somewhat stiffer that normal myocardium. Normal myocardium displays a fiber stress of 1-10 kPa.

Duration of Effect: The period for maintaining the supportive effect of the biopolymer has not been determined yet, but could be at least six months and, possibly, one year or longer.

Plasticity/Porosity. Porosity should be secondary to stiffness, concentration, or rate of degradation. However, a porosity of 300-420 µm may be adequate for cardiac tissue applications.

Biodegradation. Ideally, the material should degrade slowly in order to provide durable relief of wall stress, ventricular volume enhancement, reshaping, improvement of ejection fraction, and, in the long term, reversal of remodeling supported by native tissue re-growth. Illustratively, the substantial presence and function of the biopolymer should persist for at least six months and preferably longer.

Storage and Stability. Preferably the biopolymer may be stored at room temperature and is stable for 1 or 2 years.

Many different types of biocompatible polymers are suitable. Suitable fibrin sealants are available from a variety of manufacturers, such as Crosseal® and Quixil® fibrin sealant available from Omrix Pharmaceuticals of New York, N.Y., and HemaSeel Fibrin Sealant available from Haemacure Corporation of Sarasota, Fla. A suitable fibrin glue may also be made from cryoprecipitate, which is a source of autologous fibrinogen prepared from a subject's own plasma. Other suitable polymers include synthetic resorbable self-curing hydrogel materials. One such material is DuraSeal® sealant, which is available from Confluent Surgical of Waltham, Mass. The DuraSeal sealant is a polyethylene glycol based sealant. Another such material is CoSeal® surgical sealant, which is available from Angiotech Pharmaceuticals of Vancouver, British Columbia, Canada, and Baxter Healthcare Corporation of Fremont, Calif. The CoSeal surgical sealant is made of two synthetic polyethylene glycols or PEGs, a dilute hydrogen chloride solution, and a sodium phosphate/sodium carbonate solution. At the time of administration, the mixed PEGs and solutions form a hydrogel that adheres to tissue. Both the DuraSeal and CoSeal sealants polymerize within seconds and are broken down in the body within weeks due to hydrolysis. Other suitable polymers include cyanoacrylate glues. Other suitable polymers include polyethylene oxides ("PEO"), PEO-poly-l-lactic acid ("PLLA-PEO block copolymer"), poly(N-isopropylacrylamide-co-acrylic acid) ("poly(NIPAAm-co-Aac)"), a pluronic agent, and poly-(N-vinyl-2-pyrrolidone) ("PVP"). Other suitable polymers include polysaccharides such as cellulose. A class of materials generally known as alginates are suitable polymers. Other suitable polymer include various beads and hydrogels which may be injected alone to mechanically disrupt neuronal signaling, or with other material to administer therapeutics along with mechanical disruption. The polymer-based beads and hydrogels may contain only polymer material, or may include cells such as stem cells, fibroblasts, or skeletal cells; proteins, plasmids, or genes; growth factors in either protein or plasmid form; chemo-attractants; fibrin factor (or fragment) E; RDG binding sites; various pharmaceutical compositions; neo-tissues; or other therapeutically beneficial materials; or any combination of the foregoing. Suitable polymers for beads and hydrogels include fibrin glue, collagen, alginates, and chitosan. Other suitable polymers include hyaluronic acid, sodium hyaluronate, and other formulations, Restylane Injectable Gel available from Q-Med of Scandinavia or from Medicis Aesthetics Holdings Inc., and Synvisc hyaluronic acid available from Gensyme. The polymer materials described herein generally illustrate certain broader classes of materials, which classes may contribute additional alternatives as would be apparent to one of ordinary skill. Where a compound is herein identified in relation to one or more embodiments described herein, precursors or analogs or derivatives thereof are further contemplated. For example, material structures that are metabolized or otherwise altered within the body to form such compound are contemplated. Or, combination materials that react to form such compound are also contemplated. Additional materials that are also contemplated are those which have molecular structures that vary insubstantial to that of such designated compounds, or otherwise have bioactivity substantially similar thereto with respect to the intended uses contemplated herein (e.g. removing or altering non-functional groups with respect to such bioactive function). Such group of compounds, and such precursors or analogs or derivatives thereof, is herein referred to as a "compound agent." Similarly, reference herein to other forms of "agents", such as for example "polymer agent" or "fibrin glue agent" may further include the actual final product, e.g. polymer or fibrin glue, respectively, or one or more respective precursor materials delivered together or in a coordinated manner to form the resulting material.

Self-gelling hydrogels are a suitable bio polymer. Such self-gelling hydrogels may be formed from alginate materials in the presence of divalent cations such $Ca^{2+}$, $Ba^{2+}$, $Mg^{2+}$, or $Sr^{2+}$. Gelling occurs when the divalent cations take part in ionic binding between blocks in the polymer chain, giving rise to a 3 dimensional network. In one approach, a dual chamber syringe converging into a single lumen injection needle may be used to inject the mixed components of the alginate mixture to gel in-vivo. One component may be a sodium alginate fully solubilized in an aqueous solution such as $H_2O$. The other component may be one of the divalent cations mentioned above dispersed (preferably not dissolved) in solution. The compounds may be mixed in any suitable manner. Prior to injection, for example, a T-type adapter attached to the syringe may be set to provide mixing of the components and initiate the gelling action, and then set to allow the alginate mixture undergoing gelling to enter the lumen and to be injected into the cardiac tissue of interest. The alginate mixture may be injected immediately, or may be allowed to partially pre-cure in the syringe in order to increase the viscosity of the hydrogel prior to injection. In some instances, a pre-cured formulation may reduce the possibility that a less viscous hydrogel may diffuse or migrate away from the tissue area of interest after injection. In order to limit or minimize diffusion/migration away from the injection site, it may be beneficial to utilize alginate materials with molecular weights in excess of 300,000. In another approach, the sodium alginate solution and dispersed cation may be pre-mixed in an external mixing chamber, and aspirated into a single lumen syringe from which it may be injected into the cardiac tissue of interest. In another approach, the sodium alginate solution may be pre-mixed with an appropriate peptide (e.g., RGD or GREDVY) for covalent attachment of the peptide to the alginate prior to mixing with the divalent cations.

Advantageously, the material properties of ionically cross-linked alginate hydrogels may be controlled in various ways. Techniques that vary the molecular weight distribution for controlling and decoupling the viscosity of the pre-gel solution from the post-gel stiffness are disclosed in H. Kong et al., Controlling material properties of ionically cross-linked alginate hydrogels by varying molecular weight distribution, Mat. Res. Soc. Symp. Proc., Vol. 711, 2002, pages GG5.7.1-GG5.7.4, which hereby is incorporated herein in its entirety by reference thereto. Other techniques, some of which are applicable to polyethylene glycol or PEG materials, are disclosed in U.S. Pat. No. 6,566,406 issued May 20, 2003 to Pathak et al., U.S. Pat. No. 6,887,974 issued May 3, 2005 to Pathak, and US Patent Application Publication No. 2004/0023842 published Feb. 5, 2004 in the name of Pathak et al., all of which hereby are incorporated herein in their entirety by reference thereto.

Another example of an injectable cross-linked polymeric preparation, which in particular is an aqueous solution of a cross-linking polymer capable of maintaining a liquid state prior to deposition within body tissue, wherein it assumes a gel state, is disclosed in US Patent Application Publication No. 2006/0083721 published Apr. 20, 2006 in the name of Cohen et al., and in US Patent Application Publication No. 2005/0003010 published Jan. 6, 2005 in the name of Cohen et al., all of which hereby are incorporated herein in their entirety by reference thereto.

U.S. Pat. No. 6,063,061 issued May 16, 2000 to Wallace et al., which hereby is incorporated herein in its entirety by reference thereto, discloses the application of molecular gels to target sites in a patient's body by extruding the gel through an orifice at the target site. Wallace et al. considered the effect of the extent of cross-linking of the polymer on several functional properties of the hydrogel including extrudability, absorptiveness of surrounding biological fluids, cohesiveness, ability to fill space, swelling ability and ability to adhere to the tissue site. The extent of cross-linking of the polymeric gel composition may be controlled by adjusting the concentration of cross-linking agent, controlling exposure to cross-linking radiation, changing the relative amounts of mono- and poly-unsaturated monomers, varying reaction conditions, and the like. Moreover, properties may also be varied by mechanically disrupting the hydrogels to create multiple subunits of hydrogel having a size which enhances the ability to fill and pack a space to which it is being delivered.

US Patent Application Publication No. 2003/0211793 published Nov. 13, 2003 in the name of Bell et al., which hereby is incorporated herein in its entirety by reference thereto, discloses an injectable bio-compatible material that comprises a biopolymer fiber that is assembled from biopolymer fibrils whose axes are substantially parallel with the axis of the fiber.

Another example of a space-occupying agent is the polysaccharide sponge, examples of which are disclosed in U.S. Pat. No. 6,334,968 issued Jan. 1, 2002 to Shapiro et al., and in U.S. Pat. No. 6,425,918 issued Jul. 30, 2002 to Shapiro et al., which hereby are incorporated herein in their entirety by reference thereto.

Another suitable therapeutic agent is alginate beads coated with chitosan material, which is particularly suitable in cases where it may be desired to anchor the alginate beads to the immediate area of injection. In this case it may be desirable to overcoat the alginate beads with a coating both chemically attached to the alginate surface on the inboard side of the coating and simultaneously bonded to myocardial tissue on the outboard. Given that both the alginate surface and the myocardial tissue have negative bonding sites available, an overcoat with a positive charge density may be appropriate. Chitosan is such a material. Chitosan is a linear polysaccharide, and given its positive charge density is a bioadhesive which readily binds to negatively charged surfaces such as mucosal membranes. The chitosan overcoat may be applied by dip coating or other known procedures, wherein the chitosan may ionically bond to the available negative sites on the alginate surface. Given this, the chitosan may act as an anchor to immobilize the beads to the negatively charged myocardial tissue, giving temporary mechanical integrity at the injection site. Temporary, in the sense that the chitosan overcoat will eventually be enzymatically dissolved. "Anchoring time" may be prolonged by increasing the thickness of the chitosan overcoat. Beads and hydrogels are described in U.S. patent application Ser. No. 11/818,220 filed Jun. 13, 2007 in the name of Lee et al., and in U.S. Patent Application Ser. No. 60/813,184 filed Jun. 13, 2006 in the name of Lee et al., which are hereby incorporated herein in their entirety by reference thereto.

The properties of injectable materials may be adjusted in view of the characteristics of the interstitial compartment (spaces between individual cells and spaces between bundles of cells) to occupy space so as either to enhance thickening of the wall, or to enhance linkage between injection sites.

Implantable mechanical devices such as particles, rods, spheres, expandable small balloons, and struts may also be used as space-occupying agent. US Patent Application Publication No. 2005/0080402 published Apr. 14, 2005 in the name of Santamore et al., which hereby is incorporated herein in its entirety by reference thereto, discloses various implantable devices for stiffening the myocardium. Mechanical struts may be made of stainless steel, titanium, or other known biocompatible metals or other rigid materials, may be long or short in length, and may be implanted by techniques well known in the field of cardiac surgery. One instrument suitable for use in creating channels into which struts may be introduced uses a laser to form a channel in the wall of a patient's heart. This channel may be used to provide access for implanting a mechanical strut of the type discussed above. A suitable instrument is disclosed in U.S. Pat. No. 6,132,451 issued Oct. 17, 2000 to Payne et al., which hereby are incorporated herein in their entirety by reference thereto. Implantable mechanical devices may also be drug-eluting to administer further treatment.

Injectates and implants that swell after being placed in the myocardium are effective to enhance wall thickening without complicating administration. In particular, trauma from the injection or implantation may be minimized. Swellable polymers may be used. Moreover, firm objects such as microspheres and rods that are made of a swellable polymer which expand after implantation or injection into the myocardium may be designed for a specific expansion size, which allows for fine control over the degree of thickening of the heart wall. The speed of expansion may be controlled to manage disruption.

Rapidly growing cells and rapid growth-promoting biologics may also be used as space-occupying agent, whether natural or genetically manipulated.

Treatment of Localized Conditions

Patterns of distribution of space-occupying agent within the myocardium for global resizing may also be used or augmented to treat localized conditions such as myocardial infarctions, overt aneurysm of the ventricular wall, and mitral regurgitation. These techniques may also be used to treat localized conditions that may not yet have progressed to cardiomyopathy.

Suitable patterns include lines encircling the pulmonary veins, lines extending from the pulmonary veins to the mitral annulus, a pattern like that used for the Maze procedure, and a pattern like that used for the Corridor procedure. Suitable techniques for identifying various heart disorders such as thin walled regions or aneurysms requiring treatment may be identified by MRI, echo, and other imaging modalities. The predetermined pattern may be short struts or a matrix. A suitable matrix may be formed from crisscrossing or interlaced mechanical struts, or multiple injections. The multiple injections may be made in a regular distribution such as, for example, a two-dimensional matrix grid, or may be irregularly distributed; however, the injections generally being sufficiently close to achieve the therapeutic effect. The identified heart disorder may, or may not, be intersected, but the pattern preferably extends into normal healthy heart tissue. Where an injectable agent is used, the dose may be uniform, or if desired may change (for example, may decrease toward the apex). Where implantable devices are used, devices of different cross-section may be used so that the effective cross-section may vary along the pattern.

U.S. Patent Application Publication 2005/0271631 A1 published Dec. 8, 2005 in the name of Lee et al., which hereby is incorporated herein in its entirety by reference thereto, discloses treating cardiac tissue by injecting an injectable polymer agent into the cardiac structure such that a therapeutic mechanical scaffolding is formed within the cardiac structure itself. In particular, the injectable scaffolding agent is a fibrin glue agent and is injected into regions of damaged myocardium such as ischemic tissue or infarct. LV wall dysfunction may also be treated by injecting the scaffolding agent into the LV wall. Cell therapy may be combined with the injection of fibrin glue or other injectable polymer scaffold agent. The polymeric forms of the agent may be injectable as precursor materials that polymerize as a scaffold in-situ within the cardiac structure. In other modes, polymer agents are injected in order to provide therapeutic angiogenesis, or to induce deposition of cells within the injected area, such as by providing the polymer with fragment E or RDG binding sites, respectively.

Figure 33:
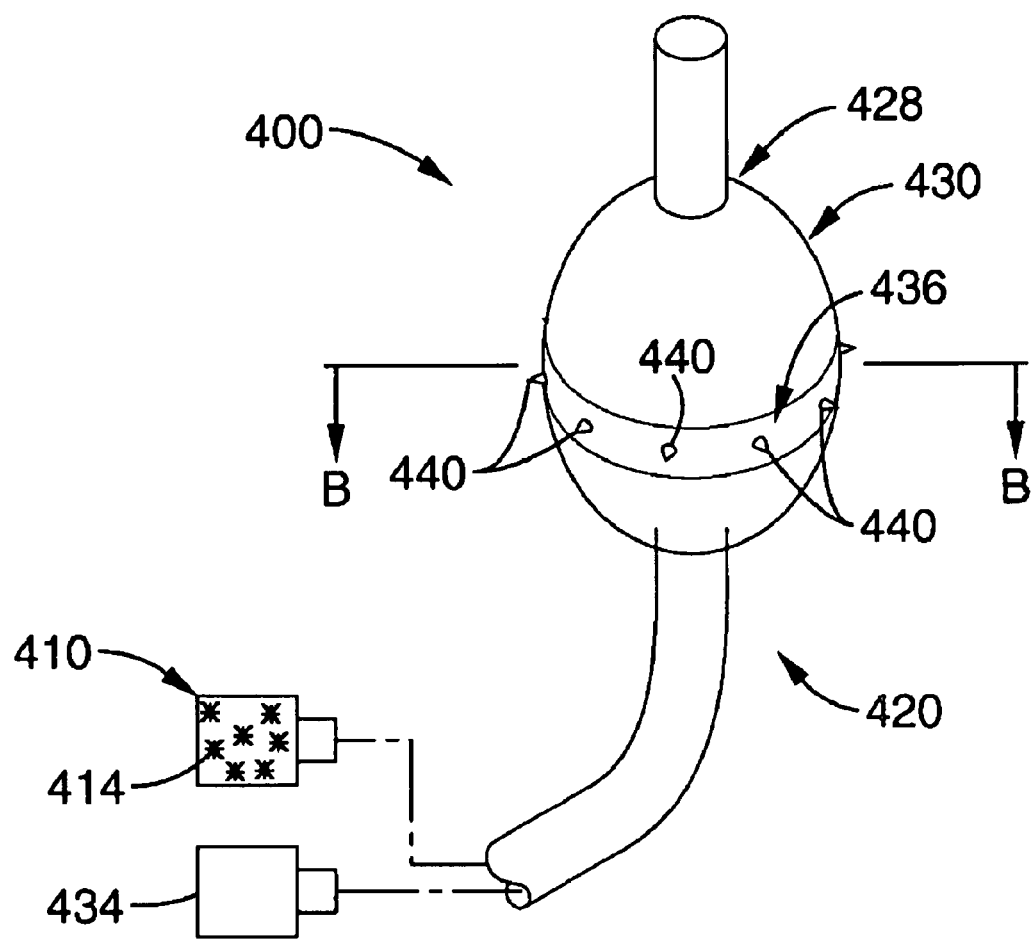
FIG. 33 is a plan drawing of an expandable balloon containing needles for injection of agent through a vessel wall to an infarct zone.

The aforementioned Lee et al. '631 published patent application also discloses a system for forming an internal molecular scaffolding to an ischemic region of a ventricle via transvascular delivery. The location may be generally at a region bordered by a vessel such as a coronary artery or vein. For example, post re-canalization of a blocked vessel, the downstream perfusion is often directly associated with infarct. Such vessel may be used to deliver an expandable balloon 400 (FIG. 33) to the infarct zone, the balloon containing needles 440 to inject through the vessel wall or in other particular modes. Moreover, other routes such as coronary sinus, or again veins may be used. In addition, such balloon may be modified for use within a ventricle, using expansion to press the needled delivery portion of the balloon against the portion of wall to be injected. In one regard, transecting a portion of a damaged cardiac tissue region may be sufficient to provide therapeutic scaffolding support, such as injecting "fingers" of scaffolding that function as ribs to support the region they span. A complete or substantially complete injection along a damaged cardiac tissue region is a highly beneficial embodiment and believed to provide for optimal results in many cases.

Figure 34:
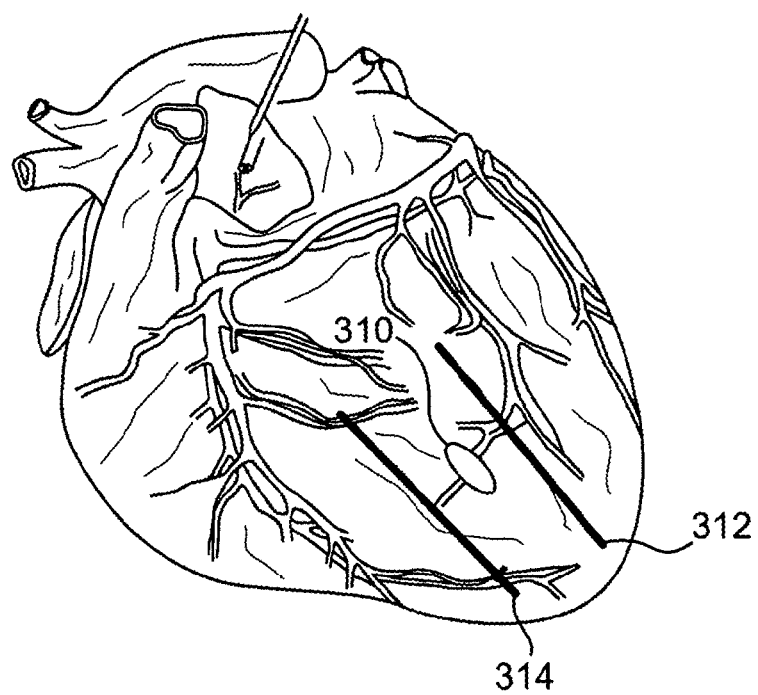
FIG. 34 is an anterior plan view of a heart on which a two longitudinal line pattern of injection sites situated on either side of an aneurysm is identified.

FIG. 34 shows a treatment where longitudinal lines 312 and 314 are run approximately parallel to one another and situated on either side of an aneurysm 310. In this configuration, longitudinal lines 312 and 314 extend only a short distance along the direction from apex to base for localized treatment. Alternatively, longitudinal lines on either side of the aneurysm may extend essentially the entire distance from apex to base. Alternatively, two circumferential lines may be situated on either side of the aneurysm 310 and extend only a short distance along the heart wall. Alternatively, two circumferential lines may be situated on either side of the aneurysm 310 and extend essentially over the entire freewall of the left ventricle.

Figure 35:
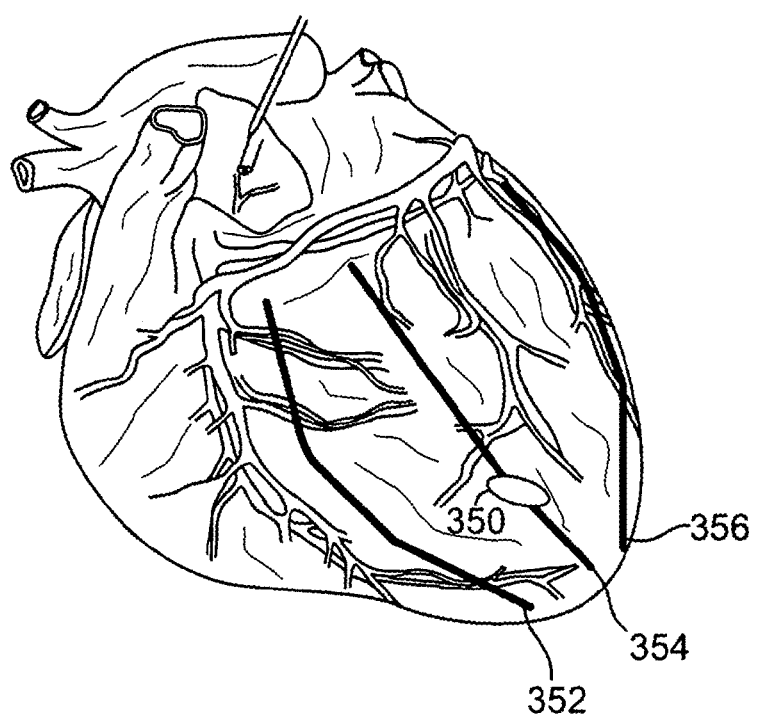
FIG. 35 is an anterior plan view of a heart on which a three longitudinal line pattern of injection sites is identified, one of which passes through an aneurysm.

FIG. 35 shows a treatment where lines 352, 354 and 356 extend essentially from the apex to the base of the heart for global resizing, but line 354 also passes through an aneurysm 350 for localized treatment. Alternatively, a longitudinal line (not shown) may span the aneurysm 350 but otherwise extend only a small portion in the direction of apex to base so that both ends are within healthy tissue. Lines for global resizing may or may not be used. Alternatively, a circumferential line (not shown) may span the aneurysm 350, and may either extend only a short distance at both ends into surrounding healthy tissue, or may extend over the ventricular free wall for global resizing and reshaping.

Figure 36:
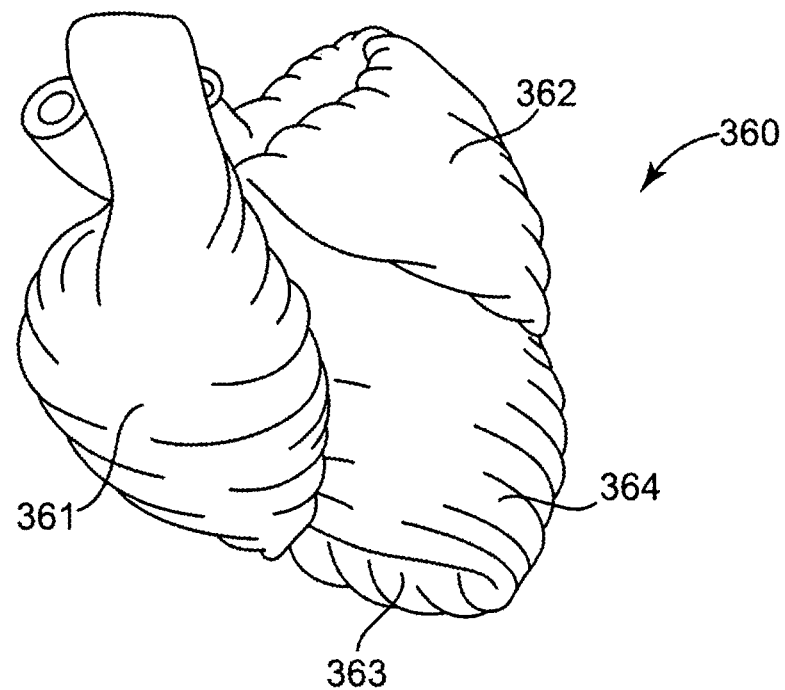
FIG. 36 is a schematic drawing of an anterior aspect of a heart in accordance with the Torrent-Guasp double loop concept.

FIG. 36 is a schematic drawing of an anterior aspect of a heart in accordance with the Torrent-Guasp double loop concept. The representation 360 shows right segment 361 of the basal loop, left segment 362 of the basal loop, descending segment 363 of the apical loop, and ascending segment 364 of the apical loop. Notice that the striations in the various segments 361, 362, 363 and 364 represent muscle fiber bundles of the myocardium. The Torrent-Guasp double loop concept is disclosed in F. Torrent-Guasp et al., Towards new understanding of the heart structure and function, European Journal of Cardio-thoracic Surgery, Vol. 27, 2005, pages 191-201, which hereby is incorporated herein in its entirety by reference thereto. The striations may be used to improve treatment in the following manner.

Figure 37:
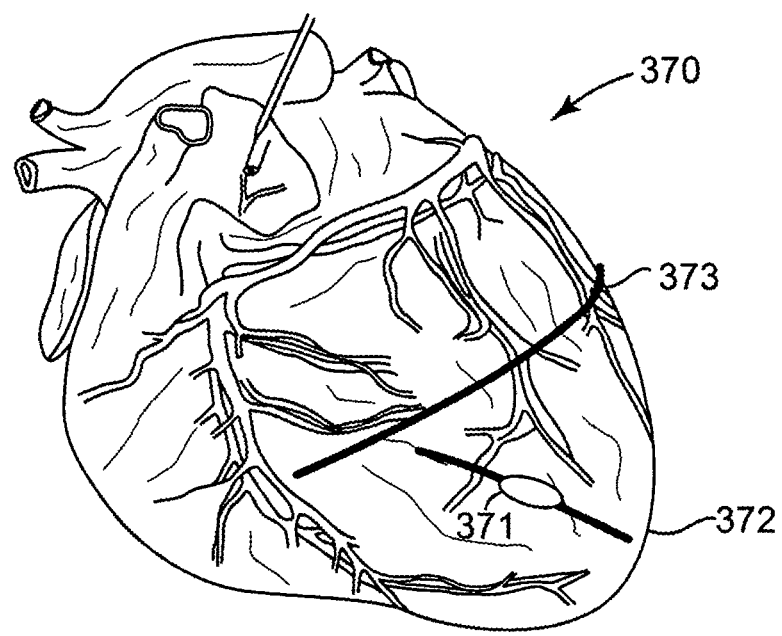
FIG. 37 is an anterior plan view of a heart on which a line parallel to striations in the myocardium extends through an aneurysm into healthy tissue on both sides of the aneurysm.

FIG. 37 shows a heart 370 that has an aneurysm 371. A line 372 extends through the aneurysm 371 into healthy tissue on both sides of the aneurysm 371. The line 372 runs in parallel with the striations, hence along the vector of maximum contraction and relaxation, to provide maximum coupling of the healthy tissue of the myocardium with the aneurysm 351 by virtue of the injections or implants made along the line 352. Inasmuch as the direction of the heart muscle fibers typically changes with depth in the myocardium, the injections or implants along the line 372 are made in the myocardium but preferably near the epicardium, rather than in the center. If desired, a circumferential line 373 with injections or implants at the center of the myocardium may be used to provide for global resizing and reshaping of the left ventricle.

For treatment of mitral valve regurgitation, for example, the mitral valve annulus may be reinforced to allow complete valve closure during ventricular contraction by the use of an injectable or implantable pattern proximate to or circumferentially encompassing part or all of the mitral valve annulus.

Figure 38:
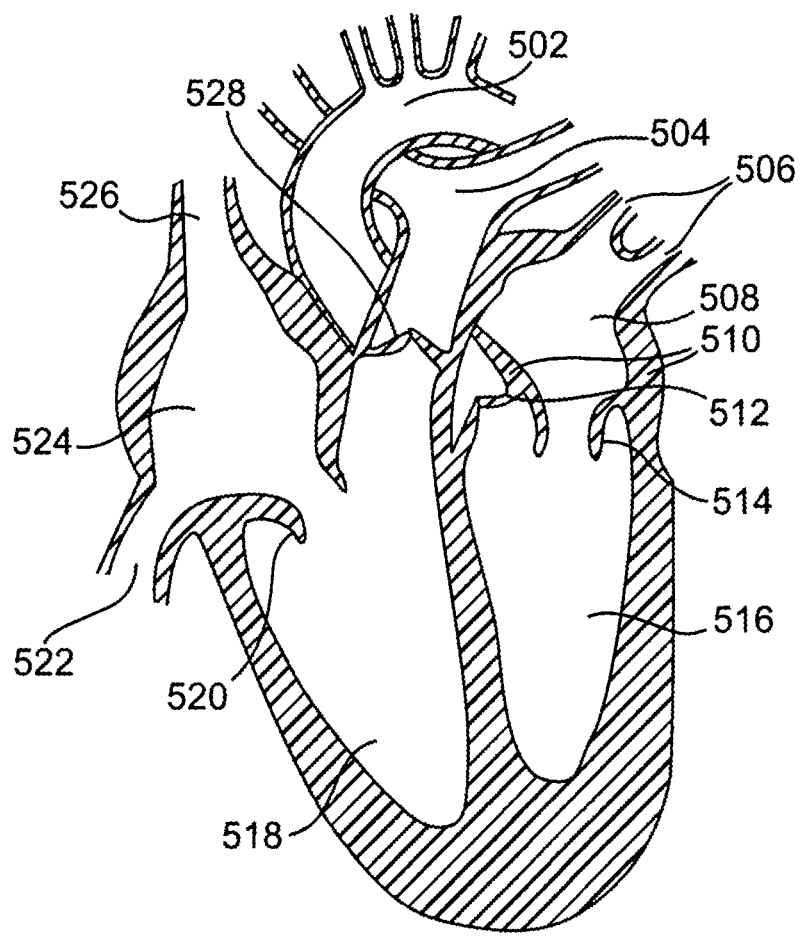
FIG. 38 is a cross section view of a human heart showing injection/implant sites near the annulus of the mitral valve, for treating mitral valve regurgitation.

Another application of utilizing space-occupying agent is in the treatment of mitral valve regurgitation, a condition in which the heart's mitral valve does not close tightly enough, thereby allowing blood to flow in the backwards direction. In this application, the space occupying agent may be utilized to re-shape the mitral valve annulus to allow the valve to more tightly close and seal off against backward flow into the left atrium while the left ventricle is undergoing contraction. FIG. 38 shows a cross section of a human heart, wherein injection/implant sites 510 near the annulus of the mitral valve are suitable for introduction of space-occupying agent to treat mitral valve regurgitation. FIG. 38 also shows aorta 502 which is the main artery taking blood to the heart, the pulmonary artery 504 which takes blood to the lungs, the pulmonary veins 506 which bring blood into the heart from the lungs, the left atrium 508, the aortic valve 512, the left ventricle 516, the right ventricle 518, the tricuspid valve 520, the inferior vena cava 522 which is a main vein that brings blood into the heart from the body, the right atrium 524, the superior vena cava 526 which is a main vein that brings blood into the heart from the head and neck, and the pulmonary valve 528. The procedure to perform the biocompatible polymer injection or the mechanical strut implant may be performed during open heart surgery wherein the mitral valve is readily exposed, or the injection procedure may be performed closed heart via a percutaneous transluminal approach through the venous system, as disclosed in U.S. Patent Application Publication 2005/0271631 published Dec. 8, 2005 in the name of Lee et al., which hereby is incorporated herein in its entirety by reference thereto. The procedure may also be performed percutaneous and epicarcially.

The description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein, including of the alternatives and equivalents of the various elements of the embodiments, may be made without departing from the scope and spirit of the invention.

The invention claimed is:

1. A method of treating a dilated chamber in a heart of a patient suffering chronic heart failure, comprising:
    introducing a biocompatible space-occupying agent into a plurality of sites within a free myocardial wall of the dilated chamber to provide a therapeutic internal structure at each of the sites;
    the therapeutic internal structures at the sites being non-contractile and distributed within the free myocardial wall with essentially no linkage with one another;
    and further being distributed in a pattern generally throughout a region of the free myocardial wall along a circumference of the dilated chamber near a widest part of the dilated chamber between an apex and a base of the dilated chamber for globally reducing stress in the free myocardial wall of the dilated chamber, and shrinking the dilated chamber at the widest part thereof.

2. The method of claim 1 wherein the pattern comprises a first line generally extending circumferentially along a major portion of a free wall of the dilated chamber.

3. The method of claim 2 wherein the first line is generally about a dilated part of the dilated chamber.

4. The method of claim 3 wherein the pattern is limited to the first line.

5. The method of claim 2 wherein the first line comprises at least three substantially evenly spaced sites.

6. The method of claim 2 wherein the first line comprises at least three sites, wherein at least some of the sites are not substantially evenly spaced.

7. The method of claim 2 wherein the pattern comprises a second line generally extending circumferentially along a major portion of the free wall of the dilated chamber, generally parallel to and spaced-apart from the first line.

8. The method of claim 7 wherein the pattern comprises a third line generally extending circumferentially along a major portion of the free wall of the dilated chamber, generally parallel to and spaced-apart from the first and second lines.

9. The method of claim 1 wherein the dilated chamber is elongated, and the pattern comprises at least two generally parallel and spaced-apart lines generally extending longitudinally along a major portion of the free wall of the dilated chamber from near the base of the heart to near the apex of the heart.

10. The method of claim 9 wherein each of the lines comprises at least four substantially evenly spaced sites.

11. The method of claim 9 wherein each of the lines comprises at least four sites, wherein some of the sites are not substantially evenly spaced.

12. The method of claim 1 wherein the dilated chamber is elongated, and the pattern comprises at least three generally parallel and spaced-apart lines generally extending longitudinally along a major portion of the free wall of the dilated chamber from near the base of the heart to near the apex of the heart.

13. The method of claim 1 wherein the space-occupying agent comprises an injectable non-living material.

14. The method of claim 13 wherein the space-occupying agent further comprises living cells, growth factors, peptides, proteins, or any combination thereof.

15. The method of claim 1 wherein the space-occupying agent comprises an injectable self-gelling alginate hydrogel.

16. A method of treating a heart having a myocardium, comprising:
    establishing a pattern of therapeutic internal structures for globally treating a ventricle of the heart of a patient suffering chronic heart failure, the pattern comprising at least one ventricular line extending generally throughout a region of a free myocardial wall of the ventricle along a circumference of the ventricle near a widest part of the ventricle between an apex and a base of the ventricle; and
    introducing biocompatible material into the free myocardial wall in accordance with the pattern to form the therapeutic internal structures;
    the therapeutic internal structures being distributed in the free myocardial wall with essentially no linkage with one another and in accordance with the pattern for globally reducing stress in the free myocardial wall and reducing systolic volume of the ventricle.

17. The method of claim 16 wherein the pattern further comprises at least one elongated line generally extending from near the base of the ventricle to near the apex of the ventricle.

18. The method of claim 16 further comprising:
    identifying an area of a heart disorder in the myocardium;
    wherein the pattern establishing step comprises establishing the pattern to have at least one intersection with the area of the heart disorder.

19. The method of claim 16 further comprising:
    identifying an area of a heart disorder in the myocardium;
    wherein the pattern establishing step comprises establishing the pattern to have a plurality of lines; and
    wherein the area of the heart disorder is disposed between at least two of the lines.

20. The method of claim 16 wherein the biocompatible material comprises an injectable self-gelling alginate hydrogel.

21. A method of treating a dilated left ventricle in a heart of a patient, comprising:
   introducing a biocompatible space-occupying agent into a plurality of sites within a free myocardial wall of the dilated left ventricle to provide a therapeutic internal structure at each of the sites;
   the therapeutic internal structures at the sites being non-contractile and distributed within the free myocardial wall with essentially no linkage with one another;
   and further being distributed in a pattern of one line which circumferentially spans around a periphery of the heart including injection sites in a series of 3-7 locations.

* * * * *